(12) United States Patent
McClellan et al.

(10) Patent No.: US 9,788,838 B2
(45) Date of Patent: Oct. 17, 2017

(54) TISSUE DEVICE

(71) Applicants: William T. McClellan, Morgantown, WV (US); Scott H. Heneveld, Whitmore, CA (US)

(72) Inventors: William T. McClellan, Morgantown, WV (US); Scott H. Heneveld, Whitmore, CA (US)

(73) Assignee: ZONE 2 SURGICAL, INC., Morgantown, WV (US)

( * ) Notice: Subject to any disclaimer, the term of this patent is extended or adjusted under 35 U.S.C. 154(b) by 389 days.

(21) Appl. No.: 14/350,874

(22) PCT Filed: Oct. 11, 2012

(86) PCT No.: PCT/US2012/059705
§ 371 (c)(1),
(2) Date: Apr. 10, 2014

(87) PCT Pub. No.: WO2013/055886
PCT Pub. Date: Apr. 18, 2013

(65) Prior Publication Data
US 2014/0296887 A1 Oct. 2, 2014

Related U.S. Application Data

(60) Provisional application No. 61/545,872, filed on Oct. 11, 2011.

(51) Int. Cl.
*A61B 17/04* (2006.01)
*A61B 17/11* (2006.01)
*A61B 17/064* (2006.01)

(52) U.S. Cl.
CPC ...... *A61B 17/1146* (2013.01); *A61B 17/0469* (2013.01); *A61B 2017/0472* (2013.01);
(Continued)

(58) Field of Classification Search
CPC ............ A61B 17/0469; A61B 17/1146; A61B 2017/1132; A61B 2017/0472;
(Continued)

(56) References Cited

U.S. PATENT DOCUMENTS

| 3,123,077 A | 3/1964 | Alcamo |
| 3,176,316 A | 4/1965 | Bodell |

(Continued)

FOREIGN PATENT DOCUMENTS

| WO | WO2011/068533 | 6/2011 |
| WO | WO2013055886 | 4/2013 |
| WO | WO2014138570 | 9/2014 |

OTHER PUBLICATIONS

Ethicon, "An Exciting New Option for Tissue Control", Stratafix Knotless Tissue Control Device, 2012; 2 Pages.
(Continued)

*Primary Examiner* — Christopher L Templeton
*Assistant Examiner* — George J Ulsh
(74) *Attorney, Agent, or Firm* — Andrew D. Wright; Roberts Mlotkowski Safran Cole & Calderon, P.C.

(57) ABSTRACT

Systems and methods for fastening tissue include a hollow element and an elongate insertion element. The insertion element has a delivery device including a cone, suture, and needle at a delivery end, and an anchor at an opposite end. The hollow element includes an engagement structure in its interior surface that permits movement of the insertion element through the hollow element in a first direction, and prevents movement of the insertion element through the hollow element in a second direction opposite the first direction. The engagement structure may include a braid or mesh that operates on a finger-trap principle. The hollow element may include an elongate element with a cone, suture, and needle at a delivery end, and an anchor at an
(Continued)

opposite end. Alternatively, the hollow element may include a button that incorporates the braid or mesh.

20 Claims, 18 Drawing Sheets

(52) U.S. Cl.
CPC ................ *A61B 2017/0647* (2013.01); *A61B 2017/1132* (2013.01)

(58) Field of Classification Search
CPC ............ A61B 2017/0647; A61B 17/08; A61B 17/122; A61B 17/11; A61B 17/04; A61F 2/08
USPC ........................................................ 606/220
See application file for complete search history.

(56) References Cited

U.S. PATENT DOCUMENTS

| | | |
|---|---|---|
| 3,541,591 A | 11/1970 | Hoegerman |
| 3,545,008 A | 12/1970 | Bader, Jr. |
| 3,570,497 A | 3/1971 | Lemole |
| 3,664,345 A | 5/1972 | Dabbs et al. |
| 3,805,300 A | 4/1974 | Tascon-Alonso et al. |
| 3,833,200 A | 9/1974 | McCombs, Jr. |
| 3,952,377 A | 4/1976 | Morell |
| 3,976,079 A | 8/1976 | Samuels et al. |
| 4,149,277 A | 4/1979 | Bokros |
| 4,301,551 A | 11/1981 | Dore et al. |
| 4,469,101 A | 9/1984 | Coleman et al. |
| 4,535,764 A | 8/1985 | Ebert |
| 4,688,561 A | 8/1987 | Reese |
| 4,741,330 A | 5/1988 | Hayhurst |
| 4,750,492 A | 6/1988 | Jacobs |
| 4,950,284 A | 8/1990 | Green et al. |
| 4,950,285 A | 8/1990 | Wilk |
| 4,971,075 A | 11/1990 | Lee |
| 4,979,956 A | 12/1990 | Silvestrini |
| 5,053,047 A | 10/1991 | Yoon |
| 5,061,283 A | 10/1991 | Silvestrini |
| 5,123,913 A | 6/1992 | Wilk et al. |
| 5,178,629 A | 1/1993 | Kammerer |
| 5,207,694 A | 5/1993 | Broome |
| 5,269,783 A | 12/1993 | Sander |
| 5,314,436 A | 5/1994 | Wilk |
| 5,318,566 A | 6/1994 | Miller |
| 5,330,489 A | 7/1994 | Green et al. |
| 5,356,412 A | 10/1994 | Golds et al. |
| 5,356,417 A | 10/1994 | Golds |
| 5,366,461 A | 11/1994 | Blasnik |
| 5,372,146 A | 12/1994 | Branch |
| 5,382,257 A | 1/1995 | Lewis et al. |
| 5,391,173 A | 2/1995 | Wilk |
| 5,403,346 A | 4/1995 | Loeser |
| 5,413,585 A | 5/1995 | Pagedas |
| 5,425,766 A | 6/1995 | Bowald |
| 5,462,542 A | 10/1995 | Alesi |
| 5,476,493 A | 12/1995 | Muff |
| 5,520,691 A | 5/1996 | Branch |
| 5,549,122 A | 8/1996 | Detweilwer |
| 5,591,206 A | 1/1997 | Moufarrege |
| 5,643,295 A | 7/1997 | Yoon |
| 5,665,109 A | 9/1997 | Yoon |
| 5,669,935 A | 9/1997 | Rosenman et al. |
| 5,683,417 A | 11/1997 | Cooper |
| 5,704,372 A | 1/1998 | Moll et al. |
| 5,725,556 A | 3/1998 | Moser et al. |
| 5,735,877 A | 4/1998 | Pagedas |
| 5,741,301 A | 4/1998 | Pagedas |
| 5,766,218 A | 6/1998 | Arnott |
| 5,810,853 A | 9/1998 | Yoon |
| 5,850,674 A | 12/1998 | Jansen |
| 5,860,948 A | 1/1999 | Buscemi |
| 5,972,006 A | 10/1999 | Sciaino |
| 5,980,557 A | 11/1999 | Iserin et al. |
| 5,984,933 A | 11/1999 | Yoon |
| 6,007,576 A | 12/1999 | McClellan |
| 6,014,792 A | 1/2000 | Marelin et al. |
| 6,015,428 A | 1/2000 | Pagedas |
| 6,063,106 A | 5/2000 | Gibson |
| 6,066,160 A | 5/2000 | Colvin et al. |
| 6,080,192 A | 6/2000 | Demopulos et al. |
| 6,083,244 A | 7/2000 | Lubbers et al. |
| 6,102,947 A | 8/2000 | Gordon |
| 6,152,895 A | 11/2000 | Wilk |
| 6,200,318 B1 | 3/2001 | Har-Shai et al. |
| 6,296,659 B1 | 10/2001 | Foerster |
| 6,432,123 B2 | 8/2002 | Schwartz et al. |
| 6,485,504 B1 | 11/2002 | Johnson et al. |
| 6,514,265 B2 | 2/2003 | Ho et al. |
| 6,695,855 B1 | 2/2004 | Gaston |
| 6,740,100 B2 | 5/2004 | Demopulos et al. |
| 6,913,607 B2 | 7/2005 | Ainsworth et al. |
| 6,926,730 B1 | 8/2005 | Nguyen et al. |
| 6,942,668 B2 | 9/2005 | Padget et al. |
| 6,951,561 B2 | 10/2005 | Warren et al. |
| 6,984,241 B2 | 1/2006 | Lubbers et al. |
| 7,008,428 B2 | 3/2006 | Cachia et al. |
| 7,226,468 B2 | 6/2007 | Ruff |
| 7,255,700 B2 | 8/2007 | Kaiser et al. |
| 7,335,215 B2 | 2/2008 | Buckman et al. |
| 7,361,179 B2 | 4/2008 | Rousseau et al. |
| 7,455,683 B2 | 11/2008 | Geissler et al. |
| 7,601,165 B2 | 10/2009 | Stone |
| 7,651,509 B2 | 1/2010 | Bojarski et al. |
| 7,708,759 B2 | 5/2010 | Lubbers et al. |
| 7,846,181 B2 | 12/2010 | Schwartz et al. |
| 7,862,584 B2 | 1/2011 | Lyons et al. |
| 7,959,650 B2 | 6/2011 | Kaiser et al. |
| 8,109,968 B2 | 2/2012 | Ashley et al. |
| 8,439,936 B2 | 5/2013 | McClellan |
| 8,480,692 B2 | 7/2013 | McClellan |
| 2002/0077631 A1 | 6/2002 | Lubbers et al. |
| 2002/0161400 A1 | 10/2002 | Demopulos et al. |
| 2002/0165561 A1 | 11/2002 | Ainsworth et al. |
| 2002/0169359 A1 | 11/2002 | McCarthy et al. |
| 2004/0059357 A1 | 3/2004 | Koseki |
| 2004/0153104 A1 | 8/2004 | Buckman et al. |
| 2004/0186515 A1 | 9/2004 | Rosenblatt |
| 2004/0193217 A1 | 9/2004 | Lubbers et al. |
| 2004/0267309 A1 | 12/2004 | Garvin |
| 2005/0085833 A1 | 4/2005 | Gedebou |
| 2005/0131430 A1 | 6/2005 | Ravikumar |
| 2005/0149122 A1 | 7/2005 | McDevitt et al. |
| 2006/0195103 A1 | 8/2006 | Padget et al. |
| 2006/0276809 A1 | 12/2006 | Oliveira |
| 2007/0021779 A1 | 1/2007 | Garvin et al. |
| 2007/0055258 A1 | 3/2007 | Hansen |
| 2008/0132943 A1 | 6/2008 | Maiorino et al. |
| 2009/0024216 A1 | 1/2009 | Cauthen, III et al. |
| 2009/0221868 A1 | 9/2009 | Evans |
| 2009/0228022 A1 | 9/2009 | McClellan |
| 2009/0259251 A1 | 10/2009 | Cohen |
| 2010/0268273 A1 | 10/2010 | Albertorio |
| 2011/0022050 A1 | 1/2011 | McClellan et al. |
| 2011/0029001 A1 | 2/2011 | Trieu et al. |
| 2012/0046693 A1 | 2/2012 | Denham et al. |
| 2012/0053630 A1 | 3/2012 | Denham et al. |
| 2012/0143349 A1 | 6/2012 | Peterson et al. |
| 2012/0203253 A1 | 8/2012 | Kubiak |
| 2012/0277770 A1 | 11/2012 | Fenton et al. |
| 2014/0128888 A1 | 5/2014 | McClellan |
| 2014/0257379 A1 | 9/2014 | McClellan |
| 2014/0296887 A1 | 10/2014 | McClellan |

OTHER PUBLICATIONS

Covidien, "Reduce Complications with V-Loc Wound Closure Device", http://ep.covidien.com/covidien-vloc-vloc...source=google&utm_, 2013; 2 pages.
Angiotech, "Quill Redefining Wound Closure", http://www.md.

(56) References Cited

OTHER PUBLICATIONS angiotech.com/focus-markets/wound-closure/quill/, 2010; 3 Pages.
"Ethicon's New STRATAFIX Knotless Tissue Control Devices", http://www.medgadet.com/2012/10/ethicons-new-stratafix-knotless-tissue-control-devices.html/print/, Oct. 5, 2012, 3 pgs.
Covidien, "Announcing . . . The V-Loc 90 Absorbable Wound Closure Device", http://web.archive.org/web/20100917152329/http://www.covidien.com/vloc/pages.aspx, Sep. 17, 2010, 1 page.
Angiotech, "Quill Device", http://www.angiotech.com/focus-markets/wound-closure/quill/, 2011; 3 Pages.
Search Report and Written Opinion dated Mar. 21, 2013 for related PCT Application No. PCT/US2012/059705, 9 pages.
Search Report and Written Opinion dated Aug. 21, 2014 for related PCT Application No. PCT/US2014/021712, 8 pages.
Su, Wei-Ren et al., The Modified Finger-Trap Suture Technique: A Biomechanical Comparison of a Novel Suture Technique for Graft Fixation, Jan. 20, 2012, Abstract, 1 page.
Office Action from U.S. Appl. No. 14/200,655 dated Jun. 24, 2016. 21 pages.
Notice of Allowance from U.S. Appl. No. 14/068,425 dated Feb. 4, 2016; 9 pages.
Office Action from U.S. Appl. No. 14/200,655 dated Aug. 26, 2015; 11 pages.
Notice of Allowance from U.S. Appl. No. 14/200,655 dated Sep. 8, 2016. 10 pages.

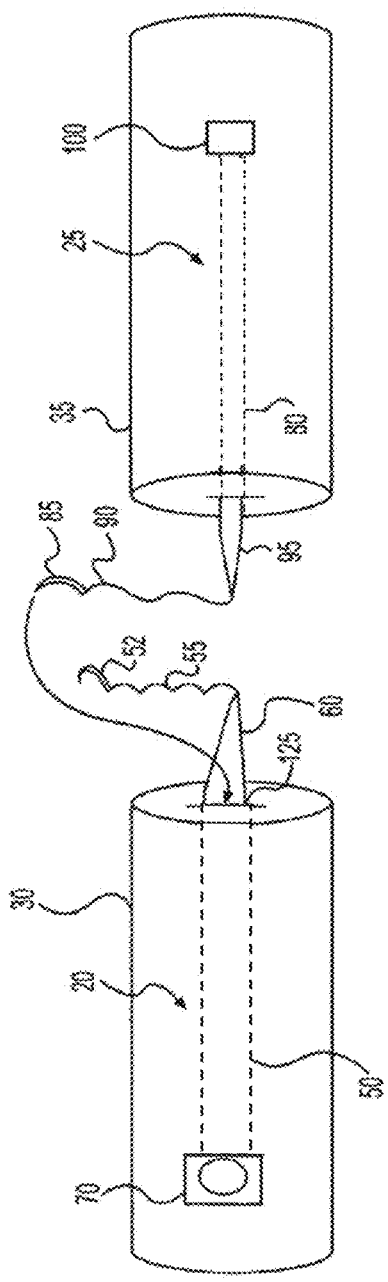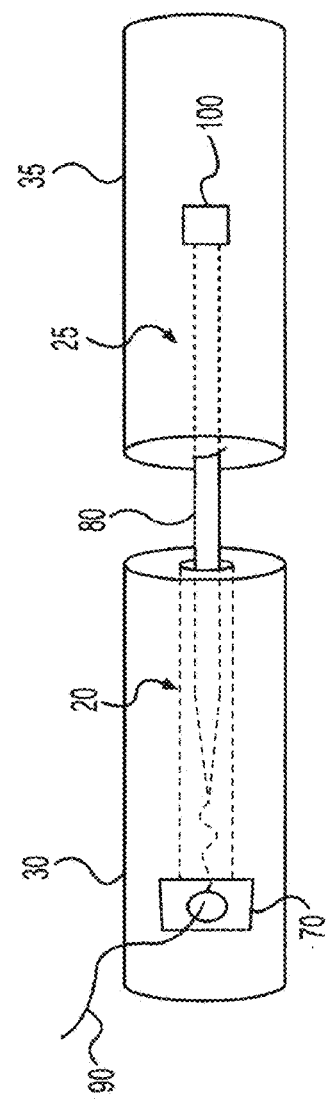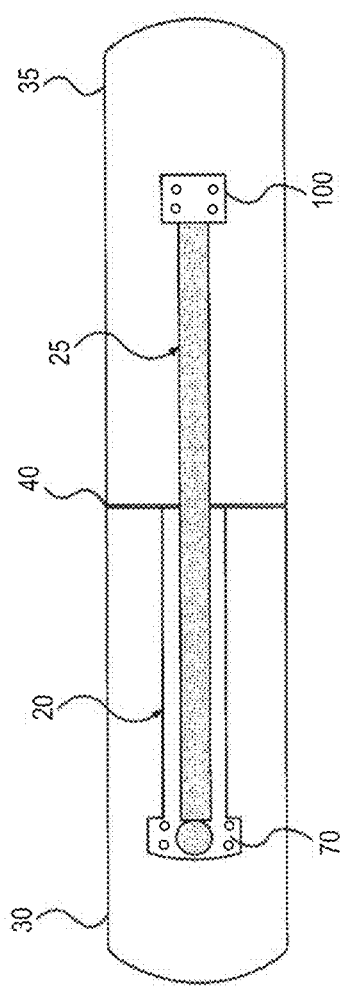

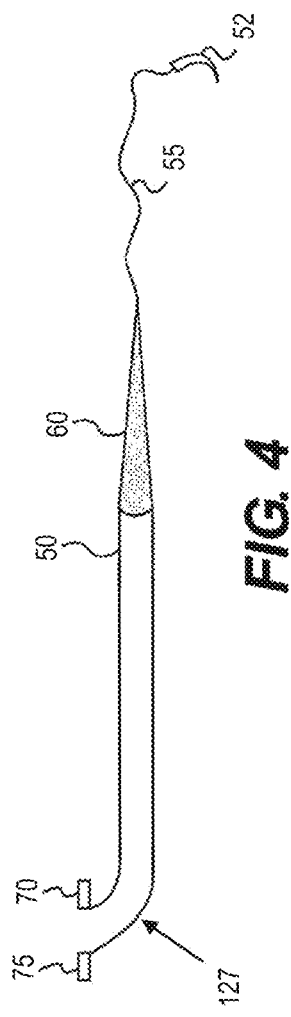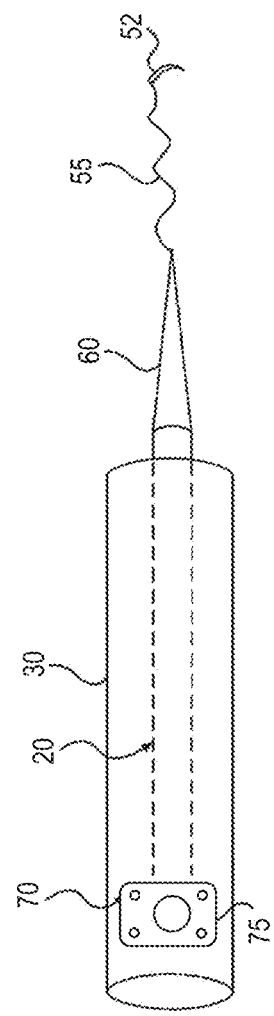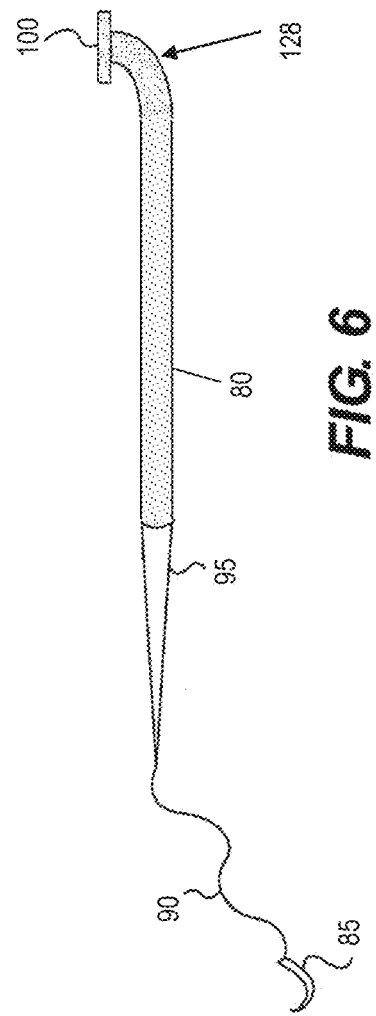

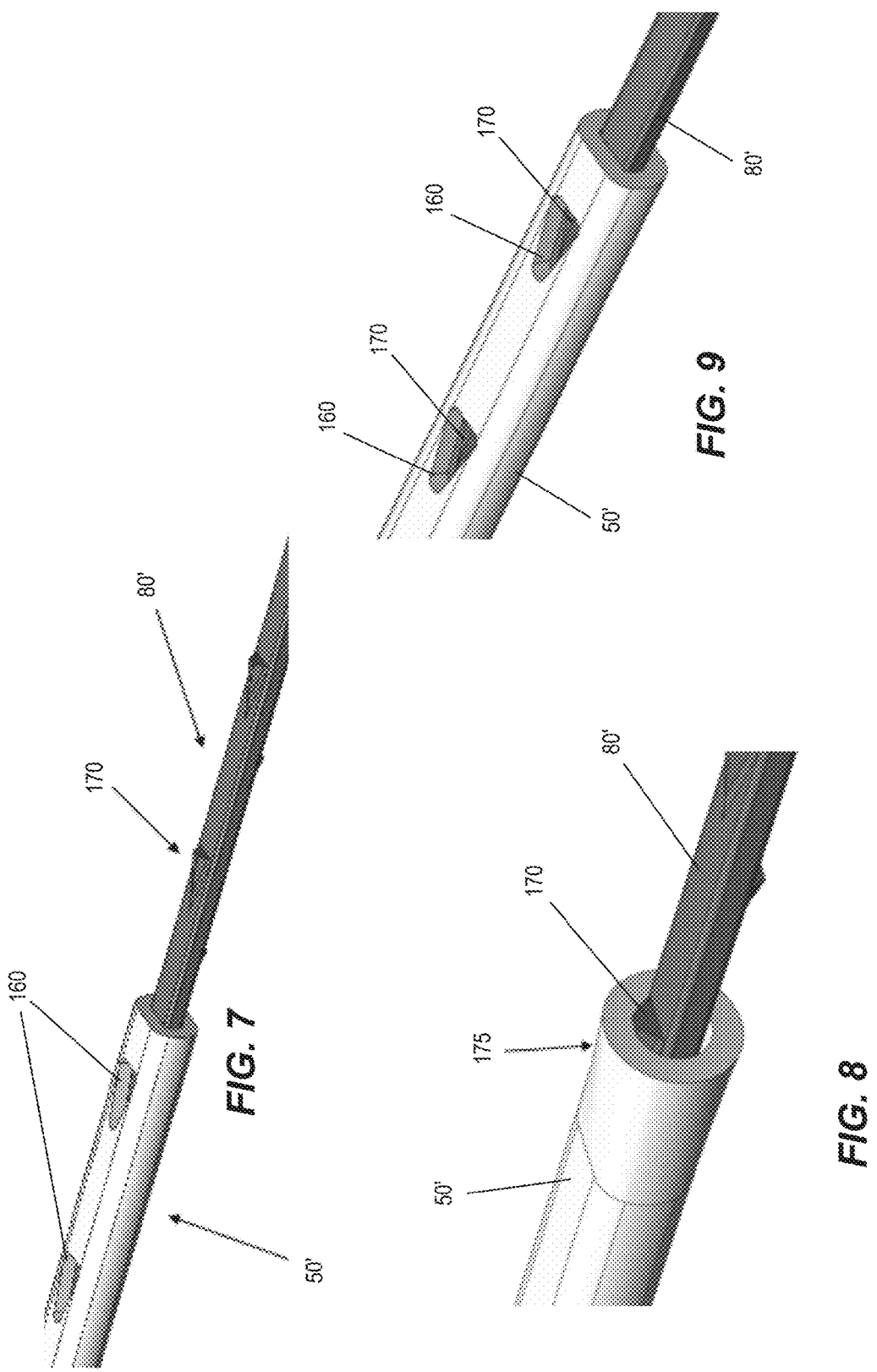

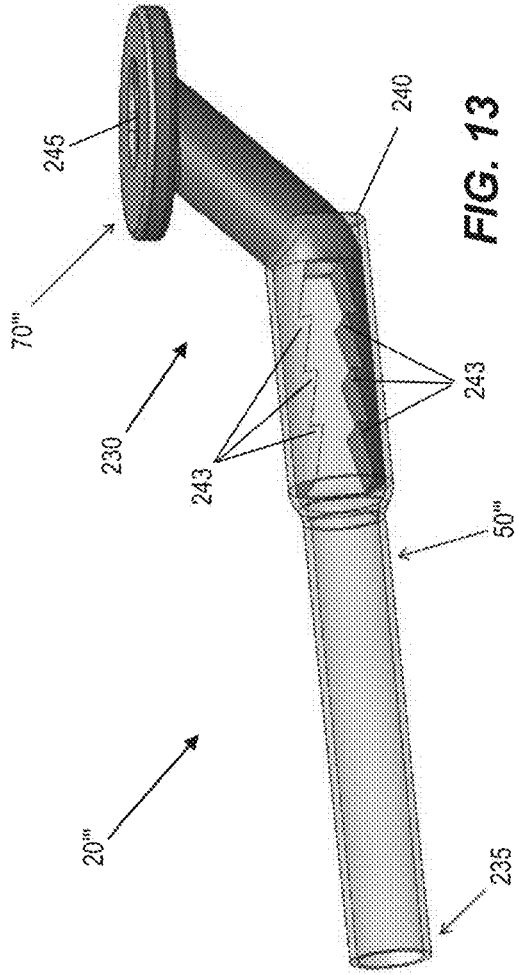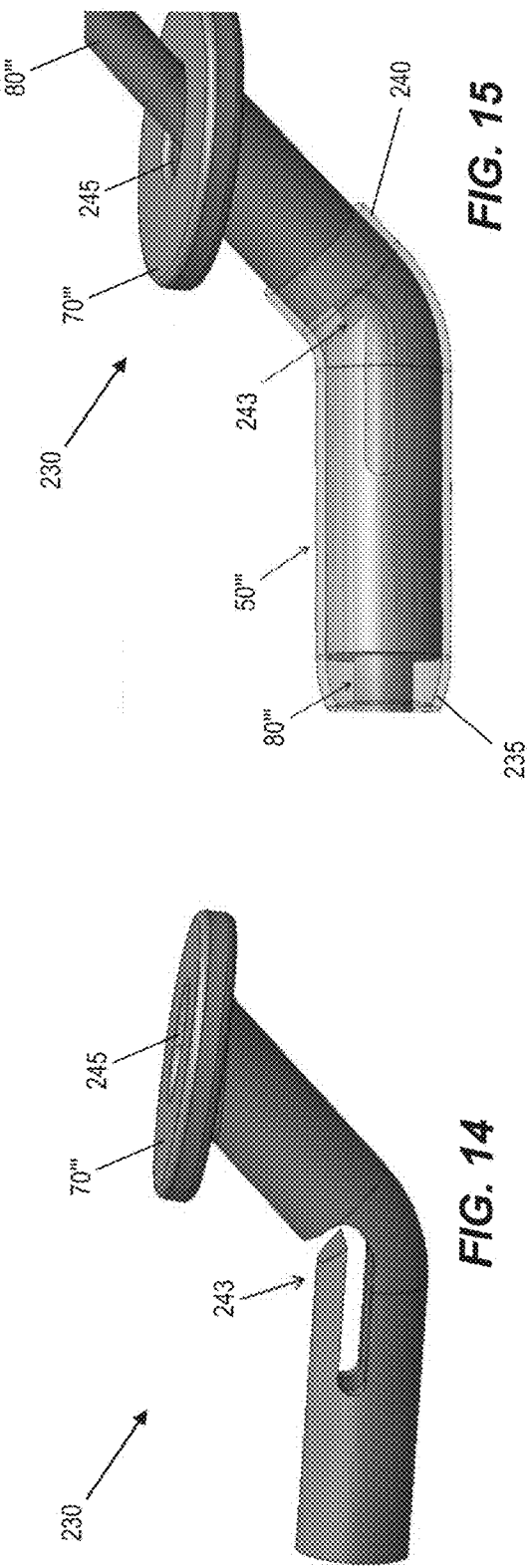

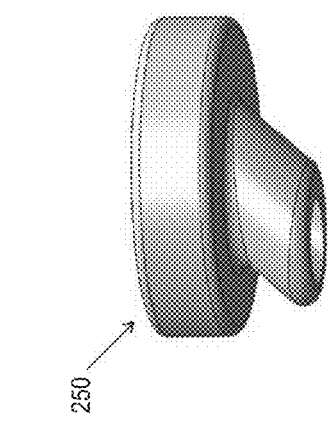
FIG. 18
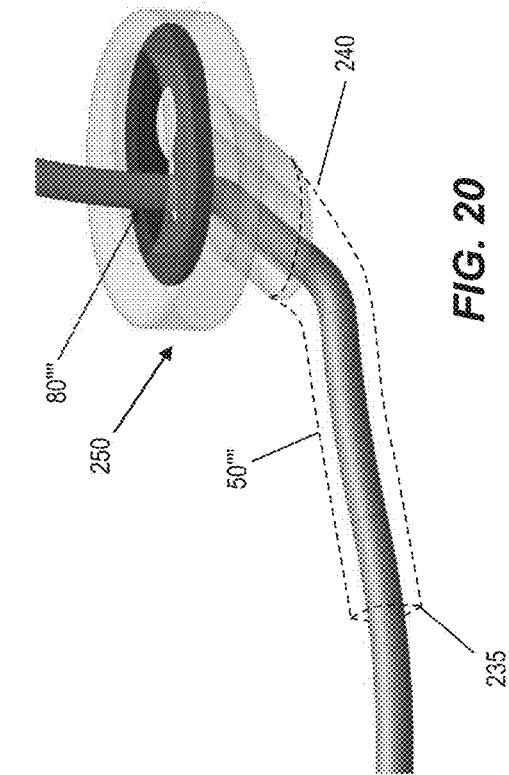
FIG. 20
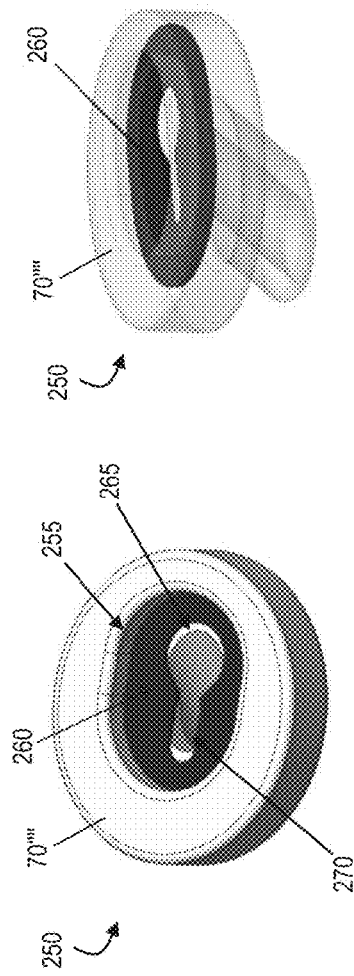
FIG. 17
FIG. 16
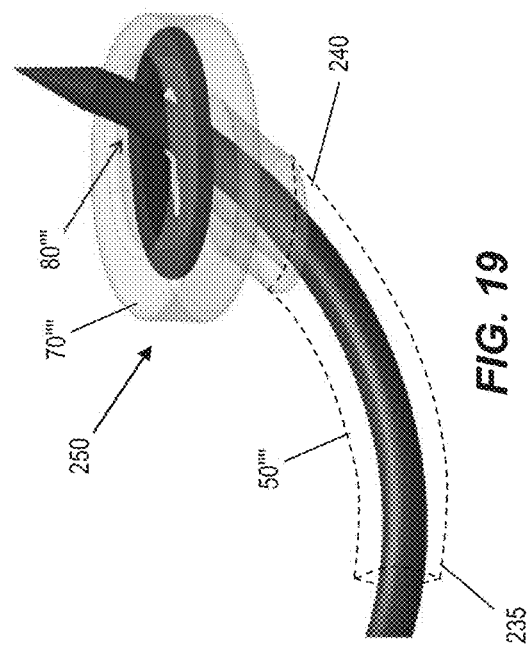
FIG. 19

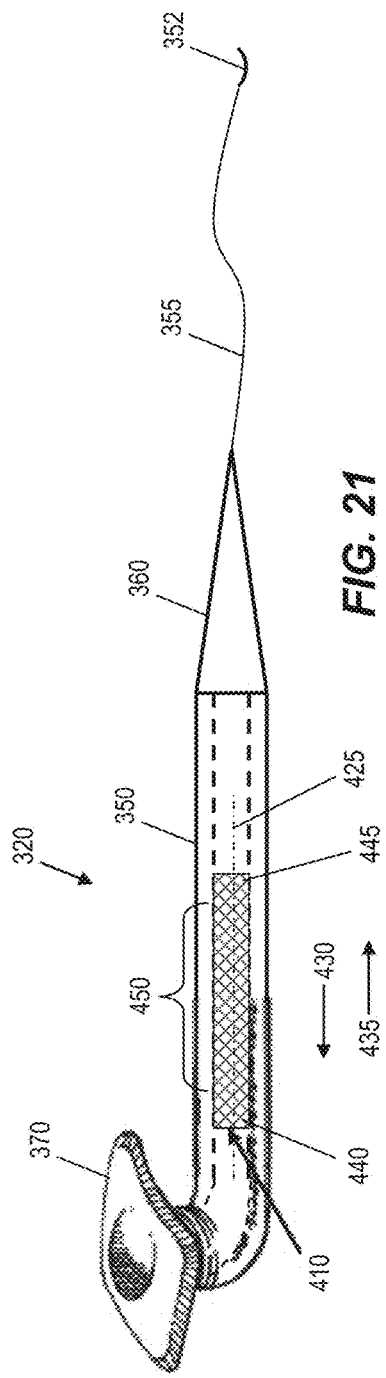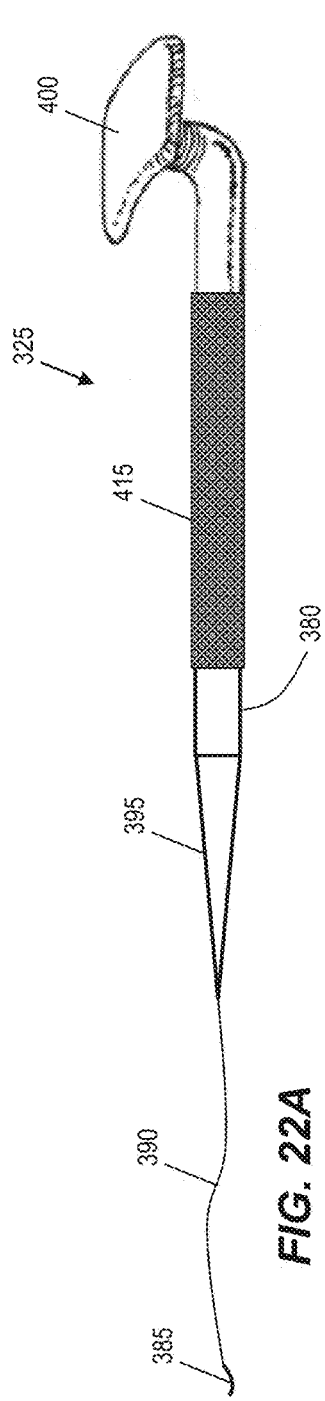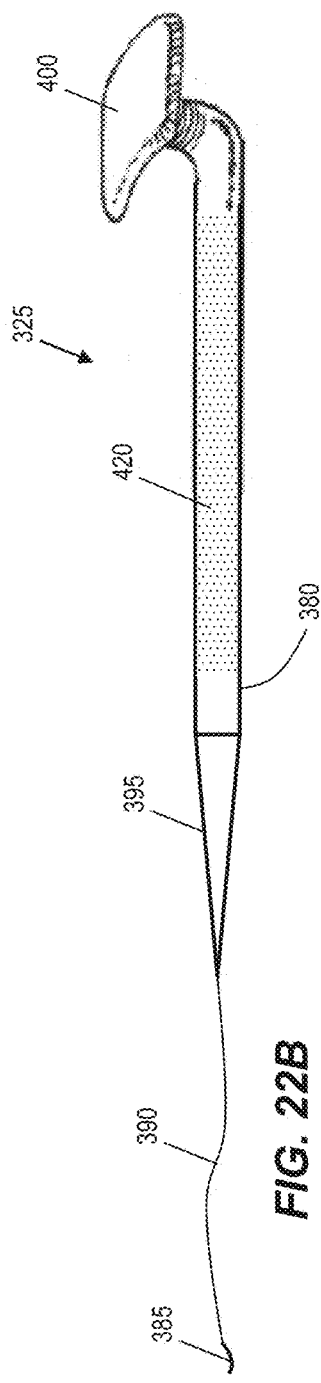

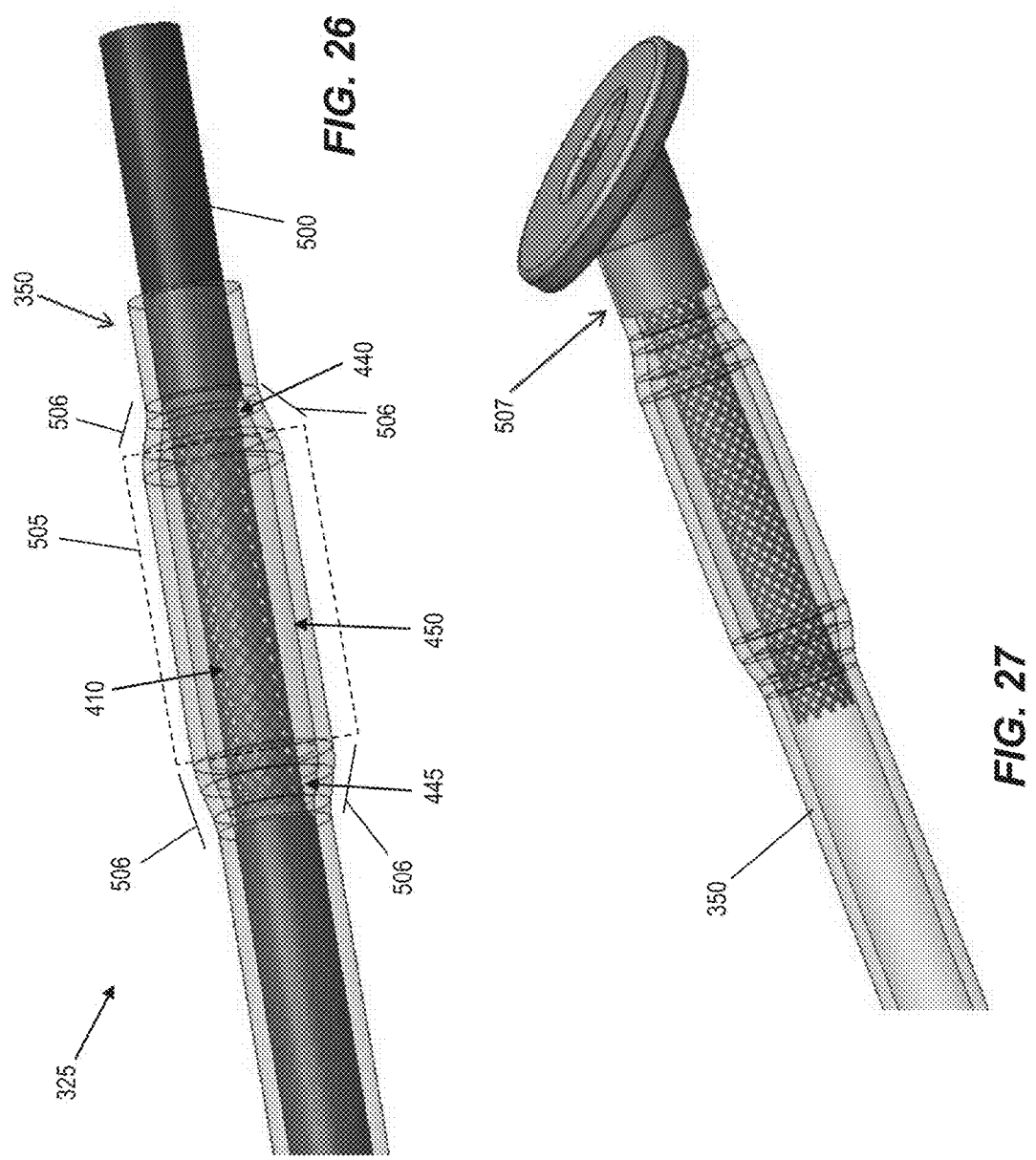

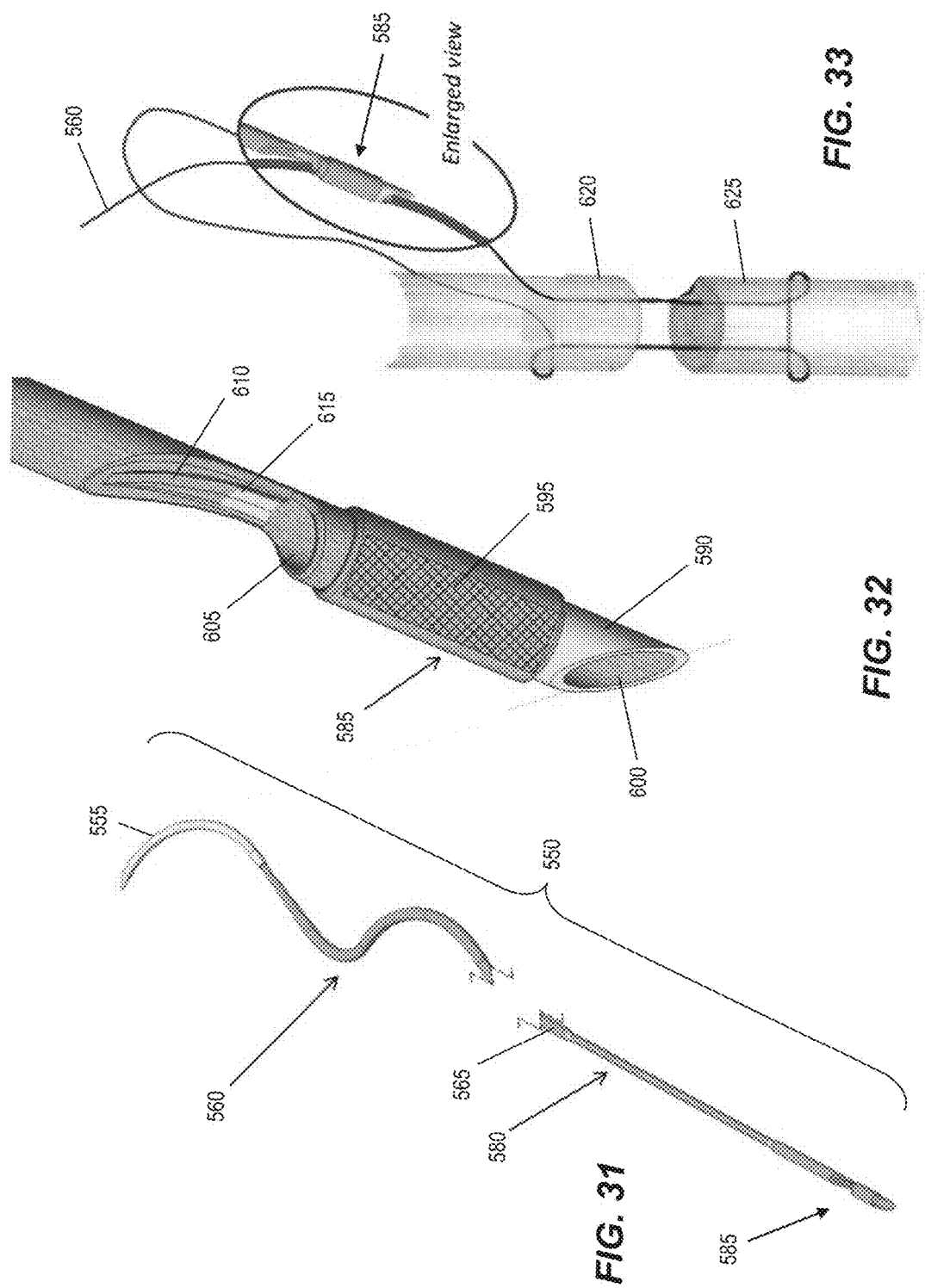

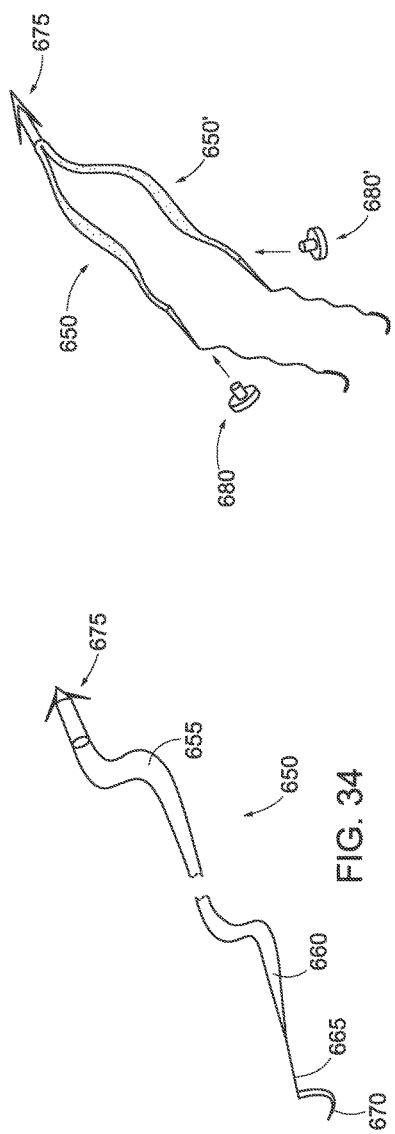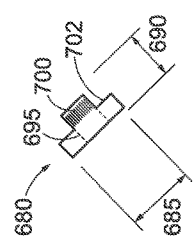

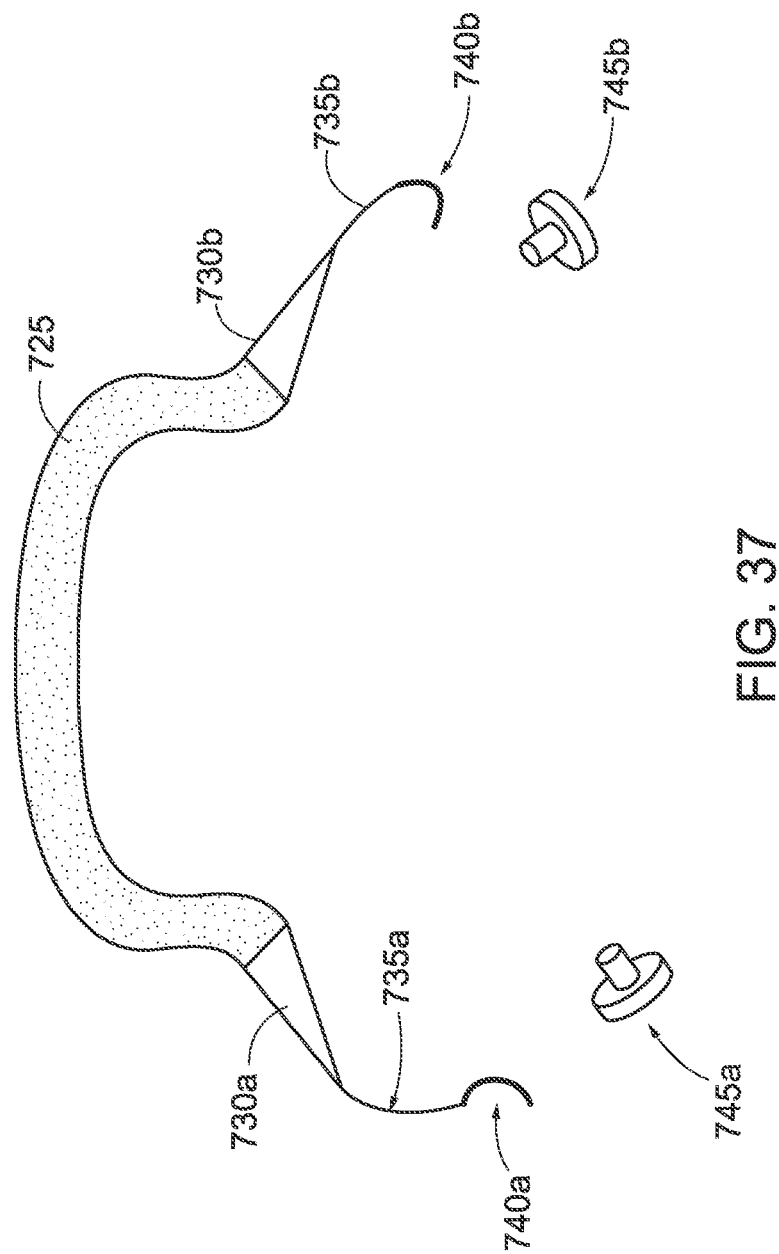

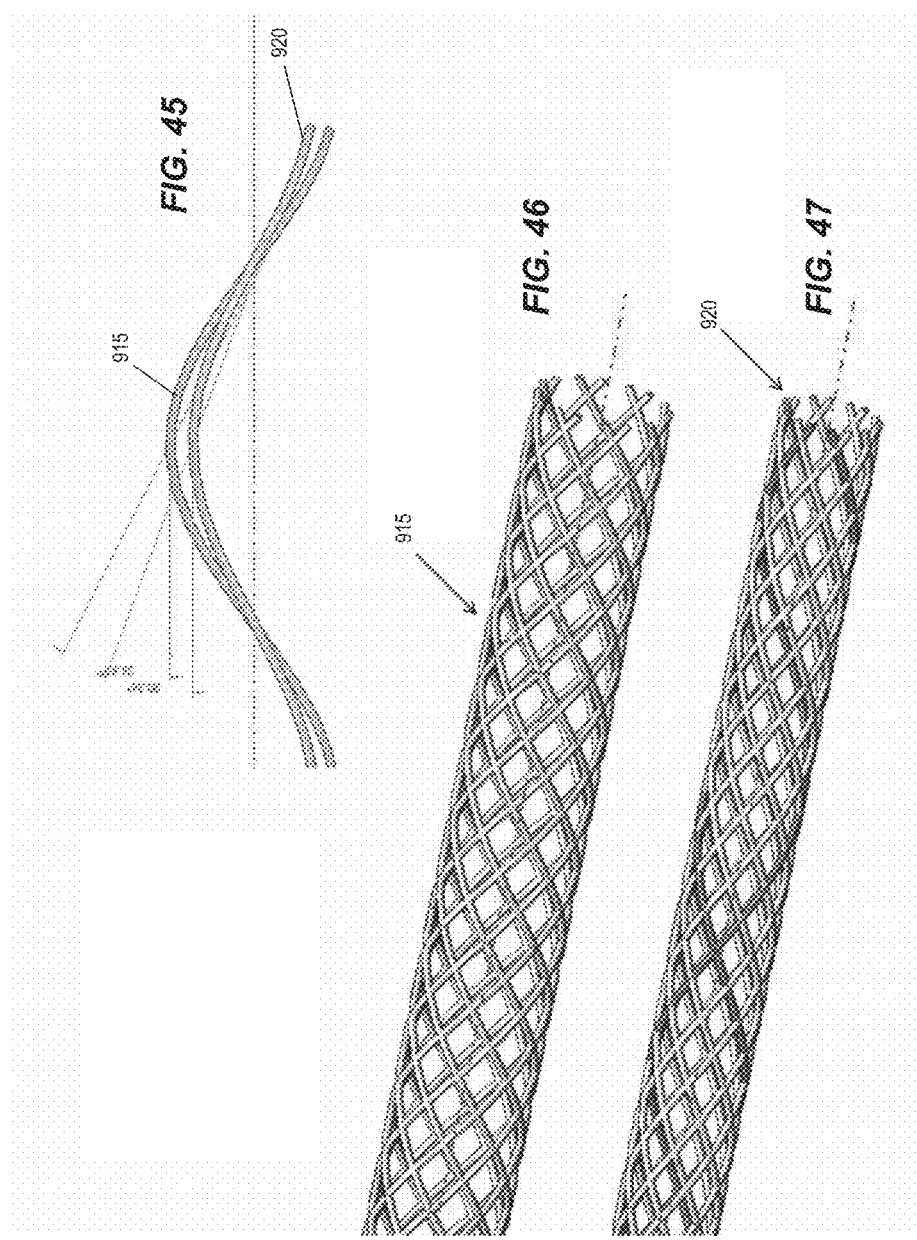

TISSUE DEVICE

CROSS REFERENCE TO RELATED APPLICATIONS

This application claims priority to U.S. Provisional Patent Application No. 61/545,872, filed Oct. 11, 2011, the contents of which are incorporated by reference herein in their entirety.

BACKGROUND OF THE INVENTION

The invention generally relates to medical devices and procedures, and more particularly to devices and methods for tendon, ligament, and soft tissue repair, closure and/or reinsertion.

Conventional methods for tendon, ligament, and soft tissue repair often involve extensive suturing of the tissue being repaired. For example, in the case of tendon repair, one known method involves passing a first suture into and out of a first portion of the tendon numerous times, resulting in two free ends of the suture extending from the cut end of the first tendon portion. A second suture is similarly arranged in a second tendon portion. The free ends of the first and second sutures are tied (e.g., knotted) together to affix the cut ends of the tendon portions together.

However, such methods have numerous drawbacks. The act of passing the suture into and out of the tendon (e.g., typically at least six times per tendon portion) causes trauma to the tendon, thereby increasing the chance for infection. Furthermore repeated trauma to the tendon by excessive handling may create excessive damage to tendon/ligament/tissue vasculature which may compromise repair. Also, the knots of the sutures artificially increase the dimension of the tendon at the repair site, which creates increased friction at the repair site and/or tendon pulley interface. Increased friction at this interface increases the opportunity for tendon failure during loading. Even further, the strength of the repair is dependent upon the knots, which may slip over time (e.g., due to surgical error). Conventional suture-based repair methods may disadvantageously impair the vascularity of the tendon and have increased tendon diameter at the repair site. Traditional suture repair requires extensive exposure, manipulation, handling, and needle penetration of the tendon.

Barbed filaments provide an alternative to knot-based repair techniques. According to known methods, a single barbed filament is passed into and out of the portions of the tendon, thereby drawings the tendon portions together. Barbs on the exterior of the barbed filament engage the tendon portions internally, thereby resisting separation of the drawn-together tendon portions. Repairs using barbed filaments can be knotless, have the potential for a lower tendon profile at the site of the repair, and have the potential for equivalent strength when compared to knot-based repairs. However, techniques using barbed filaments can be more traumatic to the tendon than traditional repairs, may increase the risk of infection and/or impair the vascularity of the tendon, and are technically demanding.

Accordingly, there exists a need in the art to overcome the deficiencies and limitations described hereinabove.

SUMMARY OF THE INVENTION

In accordance with a first aspect of the invention, there is a system for fastening tissue. The system includes a female segment comprising a hollow body, an first anchor at one end of the hollow body, and a braided capture element on an interior surface of the hollow body. The system also includes a male segment comprising an insertion element, a second anchor at one end of the insertion element, a suture and needle connected to another end of the insertion element. In an installed state, the female segment is structured and arranged to be within a first tissue with the first anchor contacting an exterior surface of the first tissue and anchoring the hollow body in the first tissue. In the installed state, the male segment is structured and arranged to be within a second tissue with the second anchor contacting the second tissue and anchoring the insertion element in the second tissue. The insertion element is structured and arranged to be inserted into and held within the hollow body in the installed state, thereby connecting the first tissue and the second tissue. The braided capture element restricts motion of the insertion element relative to the hollow body in the installed state.

In accordance with another aspect of the invention, there is a system for securing tissue. The system includes a single elongate element having a male end and a female end. The elongate element includes: a needle at the male end; a suture connected to the needle; an introducer wedge connected to the suture; an insertion element connected to the introducer wedge; and a capture tube connected to the insertion element. The capture tube is at the female end. The capture tube comprises a hollow body having a first opening and a second opening. A braided capture element is inside the hollow body.

In accordance with another aspect of the invention, there is a system for a system for repairing tissue. The system includes an elongate insertion element having a first end and a second end. The system includes a first introducer wedge, first suture, and first needle at the first end. The system includes a second introducer wedge, second suture, and second needle at the second end. The system includes a first trap button and a second trap button. Each of the first trap button and the second trap button comprises a disc-shaped element having an anchor surface, and through-hole, and an engagement structure in the through hole. Each engagement structure is structured and arranged to engage a portion of the insertion element.

In accordance with additional aspects of the invention, there is a method of tissue repair. The method includes: introducing a first segment including a delivery assembly into a first soft tissue; removing the delivery assembly to expose an opening of a hollow body of the first segment; introducing a second segment including a second delivery assembly and an insertion element into a second soft tissue; guiding the second delivery assembly through the opening; and advancing the insertion element into the hollow body, thereby joining the first soft tissue and the second soft tissue. The removing the delivery assembly includes cutting the first segment so that an opening of the hollow body is substantially flush with an end of the first soft tissue. The method may also include removing the second delivery assembly from the insertion element after one of: the guiding and the advancing. The introducing the first segment includes: inserting the delivery assembly into a sidewall of the first soft tissue, through an interior of the first soft tissue, and out of an end of the first soft tissue; and advancing the hollow body through the first soft tissue until an anchor at one end of the hollow body engages the first soft tissue. The method may also include securing the first segment to the second segment. The securing may include moving the insertion element into a braided capture element within the hollow body. The securing may also include gripping an exit end of the braided capture element to provide a resistive force that maintains the braided capture element in a compressive state while moving the insertion element into and through the braided capture element. The delivery assembly used in the method may include an introducer wedge connected to a first end of the hollow body, a suture connected to the introducer wedge, and a needle connected to the suture.

In accordance with further aspects of the invention, there is a method of manufacturing a tissue device including a braided capture element. The method includes: locating or forming a braided capture element around a mandrel; placing a hollow tube around the braided capture element; and fusing ends of the hollow tube to the braided capture element. The braided capture element may be a finger trap. The method may include placing shrink tubing around at least a portion of the hollow tube over ends of the braided capture element. The method may include placing an insulator ring over portions of the hollow tube prior to placing the shrink tubing. The fusing may include applying heat to the hollow tube. The heat softens or melts exposed portions of the hollow tube. The heat causes the shrink tubing to shrink and push the softened or melted material of the hollow tube into voids in the braided capture element. The method may include using the insulator ring to define a free-braid portion of the braided capture element that is not directly connected to (not fused to) the hollow tube. The method may include removing the shrink tubing, insulator ring, and mandrel from the hollow tube. The method may include forming an insertion element in which a portion of the length of the insertion element is partially flattened into the shape of a rounded rectangle. The flattened portion has a major dimension that is greater than the nominal diameter of the insertion element at non-flattened (e.g., circular) portions of the insertion element. The nominal diameter of the non-flattened portion of the insertion element may be substantially less than the diameter of the braided capture element, such that there is a clearance between the non-flattened portion of the insertion element and the inner surface of the braided capture element. The major dimension of the flattened portion, may be roughly the same as, or larger than, the inner diameter of the braided capture element.

In accordance with additional aspects of the invention, there is a method of tissue repair. The method includes create a running suture at plural locations in a first tissue and a second tissue using a needle and a suture of a single elongate element. The single elongate element has a male end and a female end. The elongate element includes: the needle at the male end; the suture connected to the needle; an introducer wedge connected to the suture; an insertion element connected to the introducer wedge; and a capture tube connected to the insertion element. The capture tube is at the female end. The capture tube comprises a hollow body having a first opening and a second opening. A braided capture element is inside the hollow body. After completion of the plural sutures, the needle and/or suture is inserted into the first opening, passed through the capture element, and moved out of the capture tube through the second opening. The needle and/or suture are then used to pull all of the remaining suture and the insertion element through the capture tube, which causes the first tissue and second tissue to move toward one another. When the first tissue and second tissue are sufficiently approximated, the excess portion of the suture and/or insertion element is cut at just outside the second opening.

In accordance with another aspect of the invention, there is a method of tissue repair. The method includes: passing a first needle into the cut end of the first tissue; moving the first needle in retrograde fashion through the first tissue toward the first incision; and passing the first needle through a sidewall of the first tissue at the first incision. The method also includes passing the second needle into the cut end of the second tissue; moving the second needle in retrograde fashion through the second tissue toward the second incision; and passing the second needle through a sidewall of the second tissue at the second incision. The first needle and the second needle are included in an elongate insertion element having a first end and a second end; a first introducer wedge, first suture, and the first needle at the first end; a second introducer wedge, second suture, and the second needle at the second end. Still according to the method, the first needle is cut off, the first suture is passed through the through-hole of the first trap button, and the first trap button is slid down the first suture and onto the insertion element. Still according to the method, the second needle is cut off, the second suture is passed through the through-hole of the second trap button, and the second trap button is slid down the second suture and onto the insertion element. A pusher tool may be used to advance the trap buttons along the sutures and onto the insertion element. Still according to the method, the first trap button and the second trap button are advanced along the insertion element until the first tissue and the second tissue are moved into contact with one another. Each of the first trap button and the second trap button includes a disc-shaped element having an anchor surface, and through-hole, and an engagement structure in the through hole. Each engagement structure is structured and arranged to engage a portion of the insertion element. Each engagement structure may include a braided capture element.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIGS. 1-6 show aspects of a system and method of tissue repair that is usable in implementations of the invention.

FIGS. 7-20 show aspects of devices that can be used in the aforementioned system in accordance with implementations of the invention.

FIGS. 21, 22A, 22B, and 23-30 show aspects of a systems and methods of tissue repair in accordance with aspects of the invention.

FIGS. 31-33 show an implementation of a knotless suture system in accordance with aspects of the invention.

FIGS. 34-36 show embodiments of a bone anchor system in accordance with aspects of the invention.

FIGS. 37-41 show aspects of a knotless suture in accordance with aspects of the invention.

FIGS. 43-47 depict aspects of the braided capture element used in various embodiments described with respect to FIGS. 21-42 according to aspects of the invention.

DETAILED DESCRIPTION OF EMBODIMENTS

Figure 11:
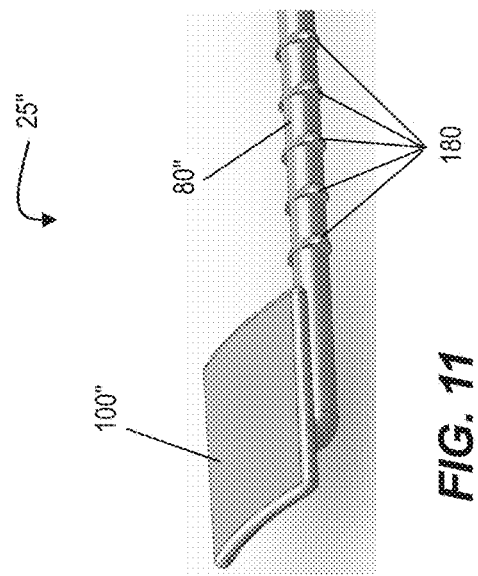

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The invention generally relates to medical devices and procedures, and more particularly to devices and methods for tendon, ligament, and soft tissue repair. Exemplary embodiments of the invention comprise two cooperating segments that, after being inserted into respective soft tissue portions, engage each other to bring the soft tissue portions into contact with one another. According to aspects of the invention, the segments may be inserted into and anchored in the soft tissue portions in a minimally invasive (e.g., atraumatically) mode. Moreover, embodiments of the invention may be used to connect soft tissue to bone, such as, for example, a ligament to bone. In this manner, implementations of the invention provide an effective system and method for soft tissue repair that overcome the above-described deficiencies and limitations of the prior art.

FIG. 1 shows a system 10 for tissue repair including a female segment 20 and a male segment 25 for repairing of soft tissue (e.g., tendon, ligament, skin, etc.). In an exemplary implementation, the female segment 20 is inserted into a first tissue portion 30, and the male segment 25 is inserted into a second tissue portion 35. As depicted in FIG. 2, the male segment 25 may be drawn into the female segment 20, which draws the tissue portions 30, 35 together. FIG. 3 shows the system 10 in a substantially completed repair position, in which female segment 20 and male segment 25 are engaged such that the first tissue portion 30 and second tissue portion 35 abut one another at an interface 40.

In embodiments, the female segment 20 includes a hollow body 50 made of permanent (i.e., not absorbed by the body) or bio-absorbable material. Non-limiting examples of permanent material include plastic, nylon, etc. Non-limiting examples of bio-absorbable include monocryl, polydioxanone (PDS), etc. However, hollow body 50 not limited to these examples, and any suitable materials may be used for forming the male and female segments. Moreover, each segment may be composed of a combination of different materials.

The female segment 20 further includes a delivery system at one end of the hollow body 50. The delivery system comprises a curved needle 52 swaged to one end of a suture 55. An opposite end of the suture 55 is integrally connected to an introducer wedge 60. The introducer wedge 60 may be in the shape of a cone (although other shapes may be used), and functions as a delivery wedge (e.g., a dilator) for atraumatically introducing the female segment 20 into soft tissue (e.g., tendon, ligament, etc.). In embodiments, the introducer wedge 60 is solid and its base has substantially the same diameter as the outer diameter of the hollow body 50. The introducer wedge 60 is affixed to the hollow body 50, for example, via a seamless connection. The introducer wedge 60 may be made of the same material as the hollow body 45, or alternatively may be made of a different material. As discussed herein, the introducer wedge 60 is configured to be cut from the hollow body 45, and the introducer wedge 60, curved needle 52, and suture are referred to as a removable delivery assembly.

In embodiments, the female segment 20 includes at least one engagement structure configured to engage an outer surface of the male segment 25. Different embodiments of the engagement structure are described in greater detail with respect to the following figures.

An end of the hollow body 50 opposite the introducer wedge 60 is provided with an anchor 70. The anchor 70 is a continuation of the hollow body 50 and comprises a flange 75 that is structured and arranged to reside outside or inside the soft tissue when the system is installed in tissue. The anchor 70 may be integral with the hollow body 50 (e.g., integrally formed via a molding manufacturing process). The anchor 70 has a hole though it which is a continuation of the interior portion of the hollow body 50. The anchor 70 is angled appropriately in relation to the hollow body 50 so that as tension is loaded on the system 10, the anchor 70 will remain low profile (with respect to the surface of the tendon) so as not to interfere with any pulley system associated with the tissue (e.g., a tendon pulley). For example, a plane of the flange 75 may be angled with respect to the longitudinal axis of the hollow body 50. As another example, a first plane containing the opening of the hollow body at the flange may be non-parallel to (e.g., intersecting with) a second plane containing the opening of the hollow body at the end opposite the flange. The angle may be provided, for example, by a bend in the hollow body 50. The bend in the hollow body 50 forms a bent end of the hollow body 50 that is bent (i.e., curved) relative to a straight end of the hollow body. In embodiments, the entire cylindrical wall of the hollow body is curved at the bend such that a portion of the cylindrical wall intersects a longitudinal axis associated with the straight end of the hollow body.

In embodiments, the anchor 70 functions to provide support for longitudinal, horizontal, and angular forces placed on the tendon/ligament system as it is loaded. The anchor 70 may or may not have small areas by which it may be sutured to the soft tissue. For example, the flange 75 may comprise one or more holes through which a suture may be passed, e.g., as shown in FIGS. 3 and 5. Additionally or alternatively, the anchor may be composed of a material that a suture can be inserted through without a pre-formed hole (e.g., pierced). The flange 75 may be any desired shape and configuration depending on the tissue, location, and anticipated load level (e.g., forces to be withstood). The anchor 70 may be made of the same material as the hollow body 50.

In embodiments, the male segment 25 includes an insertion element 80. The insertion element is preferably solid, e.g., not hollow, although any suitable construction may be used. Like the female segment 20, the male segment 25 includes a delivery system (e.g., removable delivery assembly) comprising a needle 85, suture 90, and introducer wedge 95. The introducer wedge 95 may comprise a solid cone, the base of which is affixed to an end of the insertion element 80. At an opposite end of the insertion element 80 is an anchor 100. In embodiments, the needle 85 is a curved tapered needle that is swaged to one end of the suture 90. Another end of the suture is integrally formed in (e.g., molded or melted into) an end of the introducer wedge 95. Moreover, the diameter of the base of the introducer wedge 95 equals the outer diameter of the insertion element 80. The insertion element 80, introducer wedge 95, and anchor 100 may be made of any of the aforementioned materials (or combinations of materials) described with respect to the hollow body 50. In particular embodiments, the insertion element 80 is a monofilament or multifilament element, composed of any suitable polymer(s) (e.g., PEEK, PET, nylon, etc.) and/or metal(s) (e.g., stainless steel, nitinol, etc.).

An additional engagement structure may optionally be arranged on the external surface of the insertion element 80. The additional engagement structure may comprise, for example, surface roughening, knurling, protrusions, indentations, etc. The additional engagement structure may be arranged at any desired location along the outer surface of the insertion element 80. Moreover, plural instances of the additional engagement structure may be located throughout the insertion element 80, for example, at regularly spaced (predetermined) intervals. In one example, a single additional engagement structure is arranged at one end of the insertion element 80.

In embodiments, when the insertion element 80 of the male segment 25 is inserted into the hollow body 50 of the female segment 20 in a first direction, the engagement structure of the female segment 20 engages the insertion element 80 in order to prevent the male segment 25 from being removed out of the female segment 20 (e.g., in a second direction opposite the first direction). If an additional engagement structure is also provided on the male segment 25, then this additional engagement structure may be configured to geometrically correspond to and engage the engagement structure of the female segment 20. Embodiments of the engagement structures are described in greater detail herein.

The anchor 100 of the male segment 25 is similar to anchor 70 of the female segment 20; however, there is no need for a hole in the middle of the anchor 100. Instead, the anchor 100 is substantially solid and is positioned at an appropriate angle (e.g., according to the bend in the male segment 25) to reduce the overall extratendinous and/or intratendinous profile of the system 10. Like the anchor 70 of the female segment, the anchor 100 may be of any suitable size and shape, and may be provided with holes for suturing.

In an exemplary method of using the system 10, the cut tendon, ligament, or tissue ends are freshened with a scalpel to optimize repair. The female needle 52 and suture 55 are delivered intratendinous (e.g., inserted into the sidewall of the tendon) starting at a distance of about one centimeter from the cut edge of the tissue. The needle 52 and suture 55 are passed through the interior of the tissue and passed out of the cut end of the tissue. After the suture 55 has been introduced in this manner, the introducer wedge 60 is pulled, using the suture 55, into and through the tendon or tissue with steady pressure until the anchor 70 engages the tendon or tissue and stops further advancement of the female segment 20. At this point, the female segment 20 is arranged in the tissue 30 as depicted in FIG. 1.

The female segment 20 may be cut flush in the plane of the tissue 30, for example as depicted at line 125 shown in FIG. 1. This cutting removes the introducer wedge 60, suture 55, and needle 52 from the hollow body 50. A portion of the hollow body 50 may also be removed by the cut, depending upon how far the female segment extends out of the tissue. This cutting exposes the hollow inner portion of the hollow body 50.

To deliver the male segment 25 into the other portion of 35 of the cut tissue, the male needle 85 and suture 90 are delivered in the tissue 35 in a manner similar to the delivery of the female needle and suture (e.g., inserted into the sidewall of the tissue about a centimeter back from the cut of the tissue). The needle 85 is extended out of the middle of the cut end of the tissue, and the suture 90 is pulled with steady pressure to pull the introducer wedge 95 and insertion element 80 into the tissue 35. The insertion element is pulled through the tissue 35 until the male anchor 100 engages the tissue and prevents further advancement. In this way, the male segment 25 is arranged in the tissue 35 as depicted in FIG. 1.

The needle 85 is removed, e.g., cut off of the suture 90, leaving a free end of the suture 90. The free end of the suture 90 is passed in a retrograde fashion through the exposed hollow body 50. More specifically, the free end of the suture 90 is inserted into the interior of the hollow body 50 at the cut 125. The free end of the suture 90 is advanced through the interior of the hollow body 50 until the free end of the suture 90 exits through the hole in the anchor 70. During, or after, this advancement of the free end of the suture 90, the cut ends of the tissue 30, 35 are approximated and the introducing wedge 95 is inserted into the interior of the hollow body 50 at the cut 125, as depicted in FIG. 2.

Pulling the free end of the suture 90 advances the insertion element 80 into the hollow body 50. In embodiments, advancement of the insertion element 80 into the hollow body 50 causes the engagement structure of the female segment to engage the insertion element 80, which prevents the male segment 25 from backing out of the female segment 20 (i.e., prevents the male segment from moving backward in a direction opposite the direction of advancement into the hollow body 50).

The male segment 25 is advanced into the female segment 30 until the cut ends of the tissue are well approximated and secure (see, e.g., FIG. 3). In some embodiments, a portion of the introducing wedge 95 and even the insertion element 80 may extend out of the hole in the anchor 70. Any portion of the male segment 25 extending from the hole in the anchor 70 is cut away, such that the male segment 25 is flush with the female anchor 70 to give the system the lowest profile possible on the tissue surface to minimize interference (e.g., with a pulley associated with the tendon).

In further embodiments, following cutting of the male segment 25, the end of the male segment 25 and the female anchor 70 may be additionally secured using a heat (e.g., to deform or melt at least one of the male segment and female anchor 70), adhesive (e.g., to adhere the male segment 25 and the female anchor 70), or by inserting a shim or wedge between the male segment 25 and the female anchor 70.

In further embodiments, at least one of the insertion element 80 and hollow body 50 may be provided with pores (e.g., holes) and/or indentations having dimensions suitable to allow for ingrowth of blood vessels or other connective tissue into the system 10 to improve anchoring of the bodies within the soft tissue. The pores and/or indentations may be created by laser or other suitable device or manufacturing method.

The male segment 25 and female segment 20 may be sized to any suitable dimension. In one exemplary implementation, the hollow body 50 has an outer diameter of about 1 mm to about 3 mm, and the device has a total length of about 3 cm. However, the system is not limited to these values, and any suitable dimensions may be used.

In yet further embodiments, at least one of the insertion element 80 and hollow body 50 may be immunologically or chemically enhanced to regulate, modify, or supplement tendon, ligament, or soft tissue healing. For example, at least one of the insertion element 80 and hollow body 50 may be coated or impregnated with growth hormone, antibiotic, etc.

According to additional aspects, portions of the male and female segments 20, 25 are flexible and soft, yet retain their prefabricated shape. For example, the hollow body 50, insertion element 80, introducer wedges 60, 95, and anchors 70, 100 may be made of thermoset material that is soft and flexible yet retains its shape after being initially formed. In this manner the bend 127 at one of the hollow body 50, and the bend 128 at one end of the insertion element 80 may be permanently set.

According to even further aspects, reinforcing fibers can be added to, or included in, at least one of the insertion element 80 and hollow body 50. Such fibers may be incorporated into the elements of the system to provide structural reinforcement.

In accordance with further aspects, embodiments may be used to connect soft tissue to bone. For example, a hollow body 50 may be passed through a drill hole in bone, and an insertion element 80 may be inserted into a soft tissue and then inserted into the hollow body 50. In this manner, embodiments may be used to restore a ligament-bone relationship.

In accordance with the soft tissue to bone implementation, a method may comprise: drilling a hole through a bone; inserting the delivery assembly of a hollow body through the hole in the bone; advancing the hollow body into the hole in the bone; and removing the delivery assembly to expose an opening of the hollow body. The method may further comprise steps similar to those already described herein, such as, for example: introducing and advancing an insertion element into a soft tissue; passing a delivery assembly of the insertion element through the hollow body; and advancing the insertion element into the hollow body. In this manner, embodiments provide a method for securing soft tissue to bone.

FIGS. 7-9 show an embodiment of a device in accordance with aspects of the invention. FIG. 7 shows an embodiment of the hollow body 50' that may be used with the female segment 20 in system 10 (e.g., of FIGS. 1-6). FIG. 7 also shows an embodiment of the insertion element 80' that may be used with the male segment 25 in system 10. According to aspects of the invention, the engagement structure of the female segment includes holes 160 formed in the wall of the hollow body 50'. The additional engagement structure associated with the male element includes a plurality of tabs or protrusions 170 that stick up from a surface of the insertion element 80'.

In embodiments, the hollow body 50' has a rounded rectangular shape (as shown in FIG. 7), and flexes to a circular shape 175 (as shown in FIG. 8) when a protrusion 170 is passing through the opening at the end of the hollow body 50', i.e., when the insertion element 80' is being inserted into the hollow body 50' in the manner described with respect to FIGS. 1-6. The hollow body 50' springs back to its rounded rectangular shape (as shown in FIG. 9) after the protrusion 170 has passed through the opening at the end of the hollow body 50'. The protrusion 170 may have a sloped front end that aids in inserting the insertion element 80' into the hollow body 50'. The protrusion 170 may have a substantially vertical back end (opposite the front end) that engages a corresponding surface of one of the holes 160 in the hollow body 50' to prevent backward movement of the insertion element 80' relative to the hollow body 50'. The insertion element 80' may have a cross sectional shape of a rounded rectangle with a major axis of about 0.04 inches and a minor axis of about 0.02 inches, although other sizes may be used. The interior hollow region of the hollow body 50' may have a size and shape that corresponds to the cross sectional shape of the insertion element 80' as shown in FIGS. 7 and 9.

Figure 12:
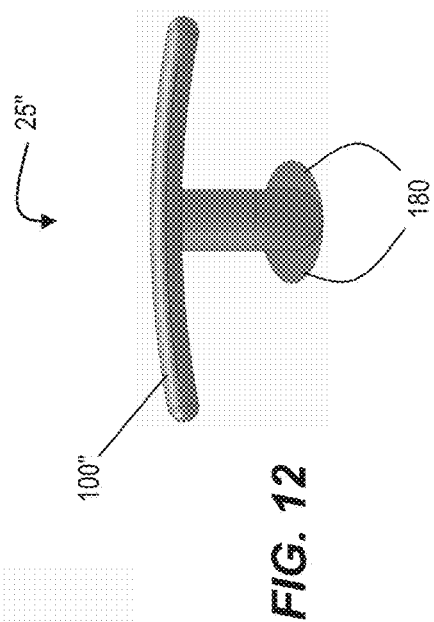
Figure 10:
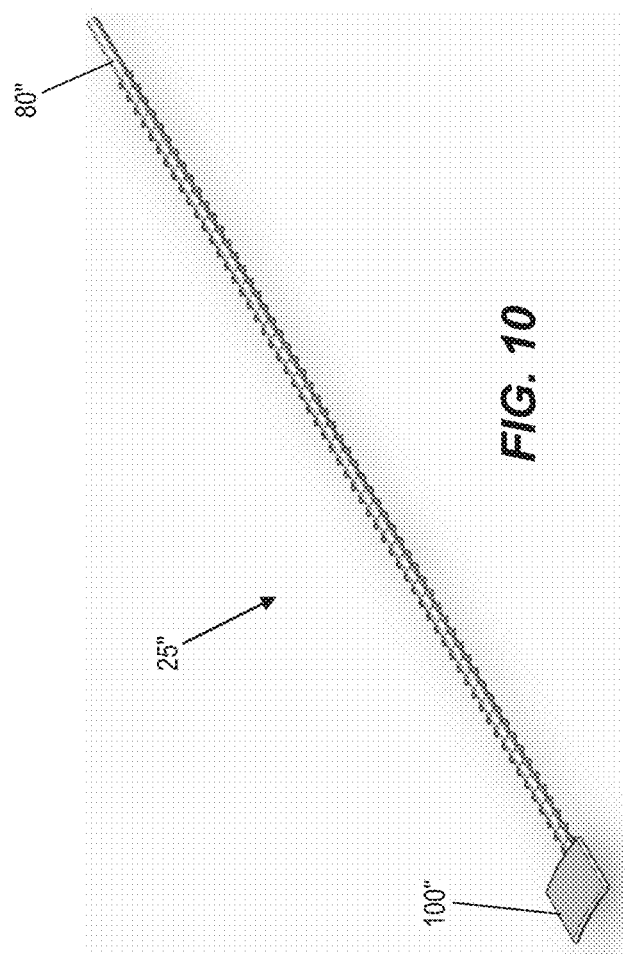

FIGS. 10-12 show an embodiment of a device in accordance with aspects of the invention. In particular, FIGS. 10-12 show different views of a male segment 25" that can be used in system 10 (e.g., of FIGS. 1-6). As shown in FIGS. 10-12, the male segment 25" includes an insertion element 80", an anchor 100" and additional engagement structures in the form of protrusions 180 that extend laterally outward from the insertion element 80".

FIGS. 13-15 show an embodiment of a device in accordance with aspects of the invention. In particular, FIGS. 13-15 show an exemplary female segment 20''' that can be used with the system 10 (e.g., of FIGS. 1-6). In embodiments, the female segment 20''' includes a hollow body 50''' and an insert 230. The hollow body 50''' includes a first end 235 with an opening that is exposed after removal of the introducer wedge, suture, and needle (not shown). The insert 230 is inserted into a second end 240 of the hollow body 50''' opposite the first end 230. The insert 230 comprises the engagement structure associated with the female segment 20''', which in this embodiment comprises at least one tooth 243. The insert 230 also includes a through-hole ending at an opening 245 at the anchor 70'''. In this manner, when the male segment and the female segment of the system 10 are being joined in the manner described with respect to FIGS. 1-6, the insertion element 80''' may be inserted into the opening at the first end 235 of the hollow body 50''', passed through the hollow body 50''' and the insert 230, and passed out through the opening 245 (e.g., as depicted in FIG. 15). When the insertion element 80''' is inside the hollow body 50''' extending from the first end 235 to the opening 245, the at least one tooth 243 bites into the insertion element 80''' and prevents backward movement of the insertion element 80''' relative to the hollow body 50''' (i.e., prevents the insertion element 80''' from being pulled backward out of the opening at the first end 235).

In the embodiment shown in FIG. 13, the at least one tooth 243 includes a plurality of teeth arranged on opposed surfaces of the insert 230 that are inside the hollow body 50'''. In the embodiment shown in FIGS. 14 and 15, the at least one tooth 243 includes a single tooth arranged at an interior portion of a bend in the insert 230. In both embodiments, i.e., FIGS. 14 and 15, the hollow body 50''' may be sized and structured to have a resilient force that compresses the portion of the insert 230 carrying the at least one tooth 243. For example, the hollow body 50''' may be composed of a stretchable (e.g., elastic) polymer material that is stretched over the insert 230 when the insert 230 is arranged within the second end 240 of the hollow body 50''', such that the stretched hollow body 50''' applies a spring-like compression force to the portion of the insert 230 carrying the at least one tooth 243. This compression force provided by the hollow body 50''' causes the at least one tooth 243 to bite into the insertion element 80''' when the insertion element 80''' is inserted into the female segment 20'''. In this manner, the insertion element 80''' need not include an additional engagement structure, although such a structure may be provided. The insert 230 may be a unitary, molded element (e.g., molded plastic) that includes at least one tooth 243 and the anchor 70'''.

FIGS. 16-20 show an embodiment of a device in accordance with aspects of the invention. In particular, FIGS. 16-20 show an alternative insert 250 that can be used with the system 10. Similar to insert 230, the insert 250 shown in FIGS. 16-20 may be inserted into the second end 240 of the hollow body 50'''' opposite the first end 235, the first end 235 being the end of the hollow body 50'''' having an opening that is exposed by removing the introducer wedge, suture, and needle from the hollow body 50"". The insert 250 also includes a through-hole ending at an opening 255 at the anchor 70"". In this manner, when the male segment and the female segment of the system 10 are being joined in the manner described with respect to FIGS. 1-6, the insertion element 80"" may be inserted into the opening at the first end 235 of the hollow body 50"", passed through the hollow body 50"" and the insert 250, and passed through the opening 255 (e.g., as depicted in FIGS. 19 and 20).

In embodiments, the insert 250 includes the engagement structure associated with the female element (e.g., female segment 20) in the form of a key-hole clip 260. A hole 265 in the clip 260 has an inner diameter larger than the outer diameter of the insertion element 80"", such that the insertion element 80"" passes easily through the hole 265 when the insertion element is being passed through the hollow body 50"" and the insert 250. The clip 260 also has a slot 270 adjacent the hole 265, wherein a width of the slot is less than the outer diameter of the insertion element 80"". The hole 265 and the slot 270 are connected and form a key-hole shaped opening in the clip 260. In operation, the insertion element 80''' is passed through the hole 265 when the insertion element is being passed through the hollow body 50"" and the insert 250 (FIG. 19). When the insertion element 80"" has been fed through to the desired extent (e.g., the tissue portions are pulled together by the system 10), the insertion element 80"" is then moved from the hole 265 into the slot 270 (FIG. 20). The smaller dimension of the slot 270 causes edges of the clip 260 to bite into the insertion element 80"", which prevents backward movement of the insertion element 80"" relative to the hollow body 50"". In this manner, the insertion element 80"" need not include an additional engagement structure (e.g., on the male segment). In an exemplary implementation, the insertion element 80"" is a nylon filament, the clip 260 is composed of metal (e.g., nitinol), and the remainder of the insert 250 is plastic that is molded around the clip 260. The invention is not limited to this configuration, however, and any suitable materials may be used.

FIGS. 21, 22A, and 22B show an embodiment of a system in accordance with aspects of the invention. In particular, FIG. 21 shows a female segment 320 including a hollow elongate body 350 (e.g., tubular body), an introducer wedge 360 (e.g., dilator), suture 355, needle 352, and anchor 370, all of which may be structured and arranged in a manner similar to female segment 20 described with respect to FIGS. 1-6, and which may be constructed using the same or similar materials as described with respect to FIGS. 1-6. Also shown in FIGS. 22A and 22B are two variations of a male segment 325 including an insertion element 380, an introducer wedge 395 (e.g., dilator), suture 390, needle 385, and anchor 400, all of which may be structured and arranged in a manner similar to male segment 25 described with respect to FIGS. 1-6, and which may be constructed using the same or similar materials as described with respect to FIGS. 1-6.

According to aspects of the invention, an engagement structure in the female segment 320 includes a braided capture element 410 inside the hollow body 350, and an engagement structure on the male segment 325 includes a relatively soft material 415 on the insertion element 380 (FIG. 22A) or a roughened surface 420 of the insertion element 380 (FIG. 22B). The braided capture element 410 comprises a tubular braid that operates in the manner of a finger trap to lock the male segment 325 to the female segment 320 when the soft material 415 or roughened surface 420 of the insertion element 380 is located inside the braided capture element 410. In embodiments, the braided capture element 410 is a helically wound braid, e.g., a biaxial braid. Applying opposing forces to the braid along its longitudinal axis 425 outward from the center of the braid increases the length of the braid while also decreasing the circumference of the braid. The length of the braid is increased by reducing the angle between the crossing fibers at their crossing points, which simultaneously reduces the radial distance from the axis 425 to the fibers, which decreases the circumference of the braid. The more the braid is lengthened along the axis 425, the more the circumference shrinks (i.e. the trap tightens).

With continued reference to FIG. 21, in embodiments, at least a first end 440 of the braided capture element 410 is connected to an inner wall of the hollow body 350. The first end 440 may be connected using adhesive, by embedding a portion of the braided element into the material of the hollow body 350, or using any other suitable connection technique. In some embodiments, a second end 445 of the braided capture element 410 is also connected to the inner wall of the hollow body 350, which leaves a free portion 450 of the braided capture element 410 that is not directly connected to the inner wall of the hollow body 350. In other embodiments, only the first end 440 is directly connected to the hollow body 350, and the second end 445 is not directly connected to the inner wall but rather is included in the free portion 450. The free portion 450 may also be referred to as a free braid or a free braid portion.

Having a free portion of the braided capture element 410 (e.g., a portion that is not directly connected to the inner wall of the hollow body 350) permits movement of a localized portion of the braided capture element 410 in the second axial direction 435 when the insertion element 380 begins to pull backward in the second axial direction 435. This movement of the localized portion of the braided capture element 410 increases a length of the localized portion of the braided capture element 410, which decreases the circumference of the localized portion of the braided capture element 410 according to the finger-trap principle, which increases the gripping force on the soft material 415 (or roughened surface 420) to prevent the soft material 415 (or roughened surface 420) from being pulled out of the braided capture element 410 in the second axial direction 435.

In embodiments, the braided capture element 410 comprises stainless steel wires braided together, although other materials may be used. The wires have a diameter of about 0.002 inches, although other sizes may be used. The braided capture element 410 may have an inside diameter of between 0.015 inches and 0.045 inches, and preferably of about 0.035 inches to about 0.036 inches, although other diameters may be used depending on the desired application. The insertion element 380 may be composed of nylon, although other materials may be used. The insertion element 380 may have a circular cross section with a diameter of between 0.25 mm and 1.0 mm, although other diameters may be used based on the inside diameter of the braided capture element 410. For example, the insertion element 380 may be a monofilament structure or a multifilament structure. The soft material 415, when used, may be any material that is relatively softer compared to the material of the insertion element 380. For example, rubber may be used as the soft material 415 when the insertion element 380 is nylon. The roughened surface 420, when used, may be any type of surface roughening, including but not limited to knurling, skiving, embossing, sanding, etc.

Figure 23:
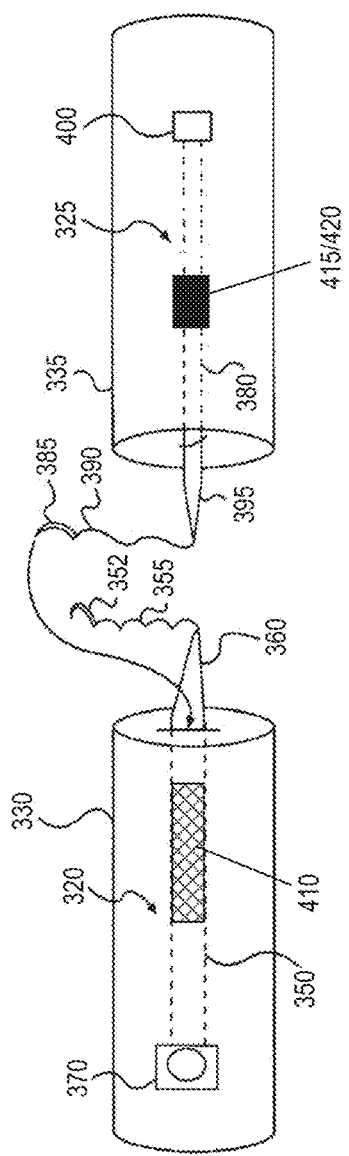
Figure 24:
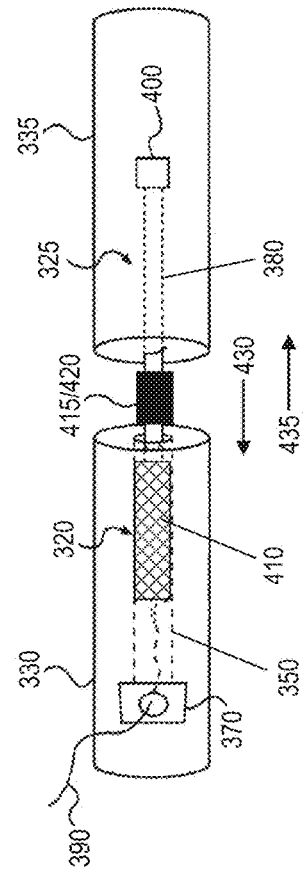
Figure 25:
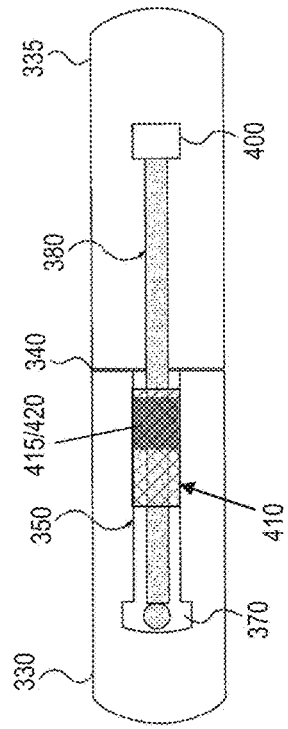

FIGS. 23-25 show the female segment 320 and male segment 325 inserted into respective first tissue 330 and second tissue 335 in a manner similar to that described above with respect to FIGS. 1-6. After the female segment 320 is placed in the first tissue 330, the introducer wedge 360 is removed (e.g., cut) from the hollow body 350 to expose an opening at the end of the hollow body 350. The insertion element 380 is then moved into and through the interior of the hollow body 350 in a first axial direction 430, which causes the soft material 415 (or roughened surface 420) to be located inside the braided capture element 410. In embodiments, the hollow body 350 is externally gripped (e.g., by forceps, fingers, etc.) at a position at, or adjacent to, the end 440 of the braided capture element 410 while the insertion element 380 is being moved into end 445 and through the braided capture element 410. Gripping at or near the exit end (e.g., end 440 in this case) provides a resistive force at a location that maintains the braided capture element 410 in a lengthwise-compressive state during the movement of the insertion element 380 there through. The soft material 415 (or roughened surface 420) is thus able to freely move into the braided capture element 410 when moving in the first axial direction 430 because such movement does not cause opposing outward axial forces on the braided capture element 410. However, when the soft material 415 (or roughened surface 420) is located inside the braided capture element 410 (e.g., as in FIG. 25), movement of the insertion element 380 relative to the hollow body 350 in the second axial direction 435 (opposite the first axial direction 430) is prevented by the finger-trap operation of the braided capture element 410. In this manner, the braided capture element 410 constitutes a locking engagement structure that permits movement of the insertion element 380 in and through the hollow body 350 in the first axial direction 430, and which prevents subsequent movement of the insertion element 380 in and through the hollow body 350 in the second axial direction 435.

In an exemplary operation of the system described herein, moving the insertion element 380 into the hollow body 350 in the first axial direction 430 causes the first tissue and second tissue to move toward one another and eventually to abut one another at an interface 340 due to the anchors 370 and 400 engaging the respective tissue portions. When the first and second tissue portions are approximated using the female segment 320 and male segment 325, e.g., as shown in FIG. 25, the braided capture element 410 prevents pulling apart of the first and second tissue by preventing the insertion element 380 from backing out of the hollow body 350. The external gripping force may be removed after the soft material 415 (or roughened surface 420) is located inside the braided capture element 410 and the first tissue and second tissue are approximated to the desired extent.

FIG. 26 depicts an exemplary method of constructing the female element 325 including a braided capture element 410 in accordance with aspects of the invention. In the exemplary method, the braided capture element 410 is placed or formed on the outside of (e.g., around) a mandrel 500, and the hollow tube 350 is placed on the outside of (e.g., around) the braided capture element 410. The hollow tube 350 may be composed of nylon and specifically Pebax, although other materials may be used. An insulator ring 505 is placed on the outside of (e.g., around) a portion of the hollow tube 350 at a central portion of the braided capture element 410, but not covering the first end 440 and second end 445 of the braided capture element 410. A shrink tubing 506 (or similar material) is then placed on the outside of (e.g., around) at least the exposed portions of the hollow tube 350, i.e., the portions of the hollow tube 350 that are not covered by the insulator ring 505. In embodiments, the shrink tubing 506 has a length grater than a length of the braided capture element 410 such that the shrink tubing covers the entire assembly. The shrink tubing 506 may be composed of any suitable heat shrinkable polymer, including but not limited to FEP (Fluorinated Ethylene Propylene). Heat is applied to the assembly to shrink the shrink tubing. In embodiments, the heat also softens or melts the exposed portions of the hollow tube 350 that are not covered by the insulator ring 505, and the shrinking of the shrink tubing 506 pushes these softened or melted portions of the hollow tube 350 into voids in the braided capture element 410, thus fusing these portions of the hollow tube 350 to the braided capture element 410. Since the ends 440 and 445 are at exposed portions of the hollow tube (e.g., are at locations not covered by the insulator ring 505), the ends 440 and 445 become fused to the inner wall of the hollow tube 350 when the heating and shrinking occurs. The portion of the hollow tube 350 that is covered by the insulator ring 505 is not shrunk, and thus the braided capture element 410 does not fuse to the hollow tube 350 at this region. In this manner, the insulator ring 505 may be used to define the free portion 450 that is not directly connected to the inner wall of the hollow tube 350 (i.e., that is not fused to the inner wall). The shrink tubing 506, mandrel 500, and insulator ring 505 are removed from the hollow tube 350 after the shrinking.

FIG. 27 depicts a similar method as FIG. 26, but with an optional insert added to one end of the hollow tube 350. As shown in FIG. 27, an insert 507 (such as insert 250 from FIGS. 16-20, or insert 230 from FIGS. 13-15 or some other insert with through-hole and an anchor/flange) may be inserted into one end of the hollow tube 350 prior to the above-described shrinking. When the hollow tube 350 is shrunk (e.g., as described with respect to FIG. 26), the hollow tube 350 tightens around the insert 507 thereby connecting the hollow tube 350 and the insert 507.

Figure 28:
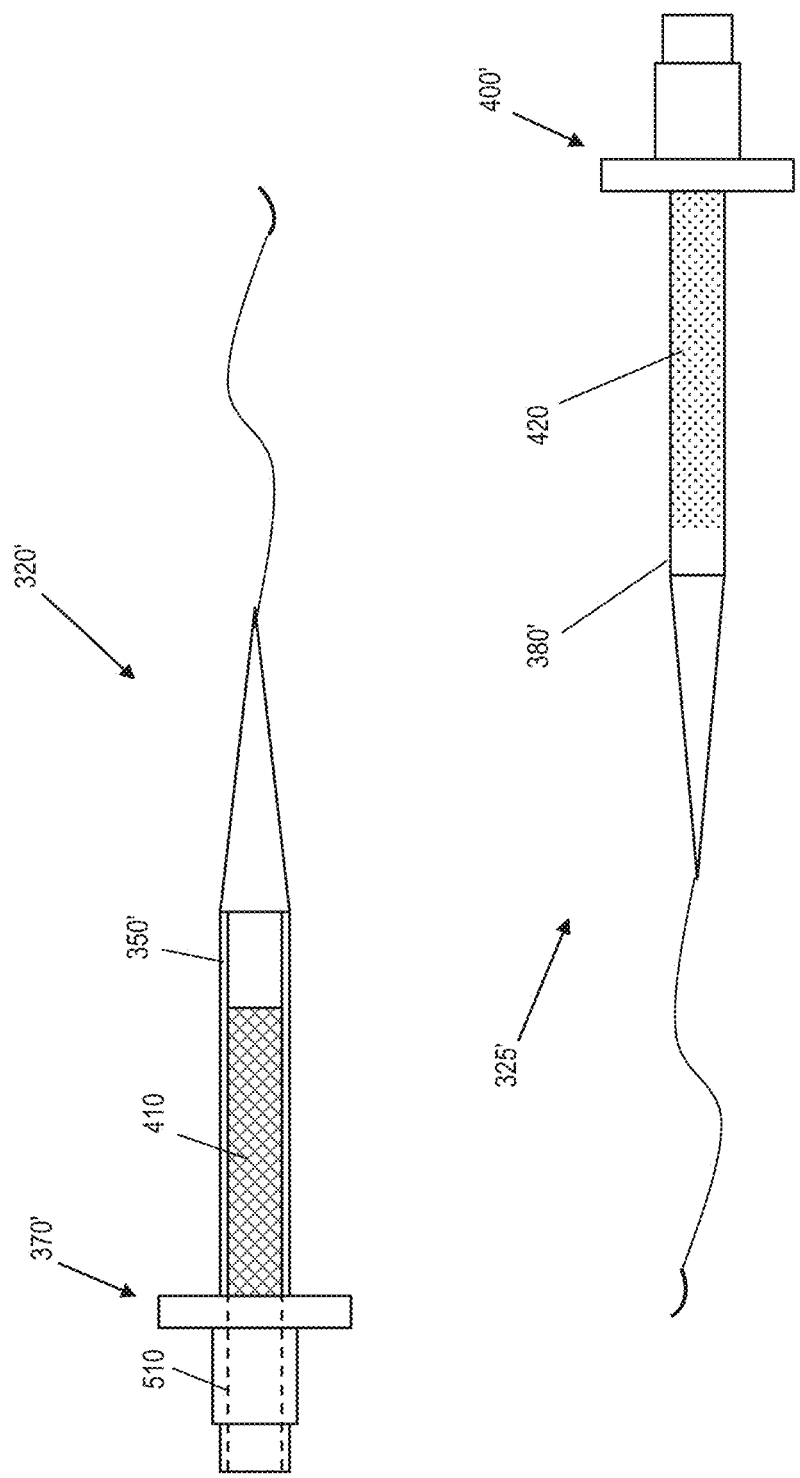

FIG. 28 shows an implementation of the female element 320' and male element 325' similar to that of FIGS. 21, 22A, and 22B. In the embodiment shown in FIG. 30C, the hollow body 350' is straight at the end connected to the anchor 370', rather than having a bend at this end as shown in FIG. 21. Similarly, the insertion element 380' in FIG. 30C also is straight at the end connected to the anchor 400' as opposed to having a bend at this end as shown in FIGS. 22A, and 22B. As with the element 320 of FIG. 21, the anchor 370' of element 320' includes a through-hole 510 aligned with the interior of the hollow body 350' such that a portion of the insertion element 380' can be passed through the entirety of the female element 320'. The anchor 370' may be swaged onto the hollow body 350', or connected to the hollow body 350' by any other suitable means. The anchor 400' does not require a through-hole, and may be a solid element that is crimped onto an end of the insertion element 380'.

As shown in FIGS. 21-28, the braided capture element 410 may extend in less than the entire length of the hollow body 350, and the soft material 415 (or roughened surface 420) may extend over less than an entire length of the insertion element 380. The ratio of the length of the braided capture element 410 relative to the length of the hollow body 350, as well as the ratio of the length of the soft material 415 (or roughened surface 420) relative to the length of the insertion element 380, may be optimized based on factors such as: manufacturing processes, strength of engagement needed between the female element 320 and male element 325, etc. Each ratio can extend to 1:1.

Figure 29:
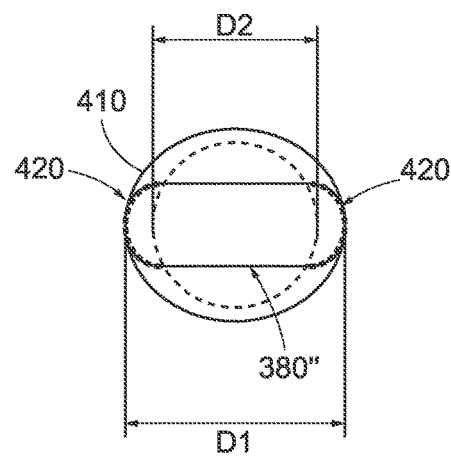

FIG. 29 shows an embodiment of the insertion element 380" in accordance with aspects of the invention. In this embodiment, a portion of the length of the insertion element 380" is partially flattened into the shape of a rounded rectangle. The flattened portion has a major dimension D1 that is greater than the nominal diameter D2 of the insertion element 380" at non-flattened (e.g., circular) portions of the insertion element 380". As depicted in FIG. 29, the nominal diameter D2 of the non-flattened portion of the insertion element 380" is substantially less than the diameter of the braided capture element 410, such that there is a clearance between the non-flattened portion of the insertion element 380" and the inner surface of the braided capture element 410. The major dimension D1 of the flattened portion, however, is roughly the same as, or larger than, the inner diameter of the braided capture element 410, which creates physical contact between the insertion element 380" and the braided capture element 410, which can cause the braided capture element 410 to constrict on the insertion element 380" when the insertion element 380" begins to move backward out of the hollow tube 350 (e.g., in the second direction 435).

Still referring to FIG. 29, surface roughening 420 may be provided at the edges of the flattened portion of the insertion element 380". One exemplary method of making the flattened portion with surface roughening 420 at the edges is to first knurl opposing portions of a round (e.g., circular) surface of a round insertion element 380", and then flatten the insertion element 380" by squeezing, e.g., in a vice. For example, a round nylon line having a diameter of 0.9 mm may be knurled in one plane, and then flattened in another plane to expose the knurl at the short-side edges of the rounded rectangle.

Figure 30:
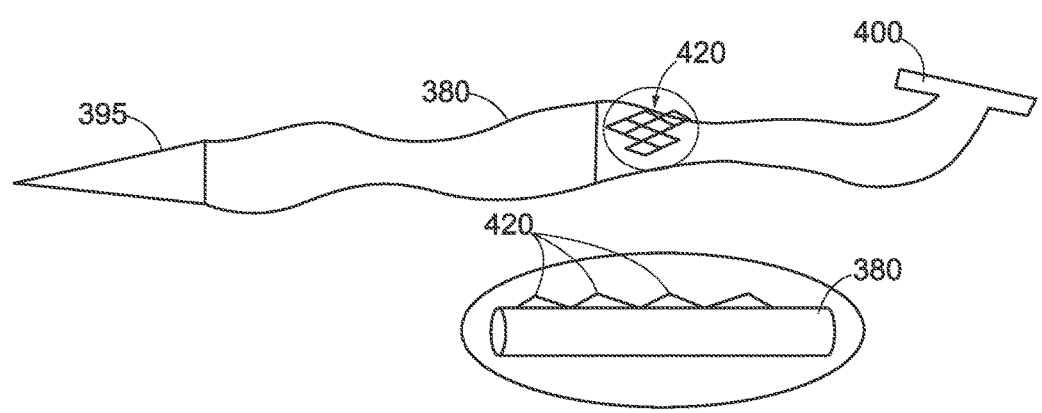

FIG. 30 depicts exemplary surface roughening 420 that may be used with the insertion element 380 (and 380', 380", etc.) in accordance with aspects of the invention. In embodiments, the surface roughening 420 is structured and arranged to provide sufficient friction for gripping the braided capture element 410 when the insertion element 380 is pulled backward out of the braided capture element 410. Additionally, the surface roughening 420 is structured and arranged to pass smoothly through bodily tissue, such as tendon, ligament, fascia, muscle, etc., without snagging, ripping, or tearing the tissue. In order to achieve the second of these functions (i.e., passing smoothly through tissue), the surface roughening 420 does not comprise barbs, corkscrews, or similar structures that would normally snag, rip, or tear tissue when being passed through the tissue. Accordingly, in embodiments, the surface roughening 420 has a structure that is produced from knurling, embossing, sanding, and other processes that produce similar type roughening. The surface roughening 420 may also be produced by molding. As shown in FIG. 30, and as described herein, the surface roughening 420 may be limited to less than the entire length of the insertion element 380, with the remainder of the insertion element 380 between the surface roughening 420 and the wedge 395 being smoother than the surface roughening 420.

FIGS. 31-33 show an implementation of a knotless suture system in accordance with aspects of the invention. With reference to FIG. 31, in embodiments, the knotless suture system includes a single elongate element 550 that has a needle 555, suture 560, and introducer wedge 565 at a first end (e.g., a male end). Connected to the introducer wedge 565 is an insertion element 580, and connected to the insertion element 580 is a capture tube 585. The capture tube 585 is at the second end (e.g., female end) of the elongate element 550 opposite the first end (e.g., the male end).

The needle 555, suture 560, and introducer wedge 565 may be similar in configuration and materials to the needle 385, suture 390, and introducer wedge 395 described with respect to FIGS. 26-28. For example, the suture may comprise a braided multi-filament suture, and more specifically may comprise a braided multi-filament including polymer fiber with metal wire.

The insertion element 580 may be similar in configuration and material(s) to the insertion element 380 described with respect to FIGS. 26-30E. For example, the insertion element 580 may comprise a polymer filament with a surface roughening (e.g., similar to surface roughening 420). In a particular example, the insertion element 580 may comprise a collapsed and over-molded multi-filament.

As shown in FIG. 32, and according to aspects of the invention, the capture tube 585 includes a hollow body 590 with a capture element 595 arranged on an interior wall of the hollow body 590. The hollow body 590 may be similar to the hollow body 350, and the capture element 595 may be similar to the braided capture element 410. For example, the hollow body 590 may comprise a polymer tube and the capture element 595 may comprise a tubular steel braid having at least one of its ends fused to the interior wall of the polymer tube and a free braid portion that is not directly connected to the polymer tube. Alternatively, the capture element 595 may comprise another type of engagement structure other than a braided structure.

Still referring to FIG. 32, the distal end of the capture tube 585 includes a first opening 600 that provides access to the interior of the capture element 595. The proximal end of the capture tube 585 includes a second opening 605 that also provides access to the interior of the capture element 595. In accordance with aspects of the invention, the knotless suture system is structured and arranged such that the insertion element 580 enters the capture tube 585 at the first opening 600, passes through the capture element 595 moving in a first direction (i.e., from the first opening 600 toward the second opening 605), and exits the capture tube 585 at the second opening 605. Utilizing the same finger-trap principle as with braided capture element 410 and insertion element 480, the capture element 595 securely engages the solid element 580 and prevents the solid element from backing out of the capture tube 585, i.e., prevents movement of the solid element 580 relative to the capture tube 585 in a second direction opposite the first direction.

In embodiments, the first opening 600 is provided by an angled cut of the hollow body 590, i.e., in a plane that is not perpendicular to a central longitudinal axis of the hollow body 590. The angled cut facilitates locating the first opening 600 with the needle 555 (or suture 560 if the needle has been removed) when first inserting the male end of the elongate element 550 into the first opening 600. The angled cut also facilitates pushing the capture tube 585 into the tissue during completion of the suture.

With continued reference to FIG. 32, the second opening 605 may be provided as a dugout portion of the hollow body 590. The dugout portion may be shaped with a curved surface 610 that guides the needle 555, suture 560, and/or insertion element 580 as they are exiting the second opening 605. Reinforcing structure(s) 615 may be provided at the thinned portion of the hollow body 590 at the dugout, such as fibers, etc.

FIG. 33 depicts an exemplary operation of the knotless suture system in accordance with aspects of the invention. The needle 555 and suture 560 may be used to create a running suture at plural locations in a first tissue 620 and a second tissue 625, which may be portions of a cut tendon, for example. After completion of the plural sutures, the needle 555 is inserted into the first opening 600, passed through the capture element 595, and moved out of the capture tube 585 through the second opening 605. The needle 555 and/or suture 560 are then used to pull all of the remaining suture 560 and the insertion element 580 through the capture tube 585, which causes the first tissue 620 and second tissue 625 to move toward one another. When the first tissue 620 and second tissue 625 are sufficiently approximated, the excess portion of the suture 560 and/or insertion element 580 is cut at just outside the second opening 605. According to aspects of the invention, the capture element 595 prevents the insertion element from backing out of the capture tube 585, such that a secure running suture is provided without having to tie any knots. After approximating the tissue, the capture tube may be left outside the tissue or may pushed through the sidewall of the tissue and housed within the tissue. For example, a knot pusher tool may be used to advance the capture tube 585 through a tendon sidewall and into the inner portion of the tendon.

It is noted that the invention is not limited to the exemplary use described with respect to FIG. 33. For example, the knotless suture system may be used to secure other types of tissue, and is not limited to use with two portions of a tendon. Also, different types of running sutures may be provided, or alternatively the system can be used to provide a single suture between two tissues. Additionally, the insertion element 580 may be advanced through the capture tube 585 by holding the insertion element 580 still and pushing the capture tube 585 along the insertion element 580, or by a combination of pulling the insertion element 580 and pushing the capture tube 585. Moreover, the needle 555, needle 555 and suture 560, or needle 555 and suture 560 and wedge 565 may be removed (e.g., cut off the remainder of the elongate element 550) prior to passing the insertion element 580 through the capture tube.

FIGS. 34-36 show embodiments of a bone anchor system in accordance with aspects of the invention. In particular, FIG. 34 shows a male segment 650 including an insertion element 655, introducer wedge 660, suture 665, and needle 670, which may be similar to the insertion element, introducer wedge, suture, and needle already described herein. For example, the insertion element 655 may comprise a monofilament or multifilament material, and may have a surface roughening similar to the surface roughening 420. A bone anchor 675 is connected to an end of the insertion element 655 opposite the introducer wedge 660, the bone anchor being structured and arranged to be inserted into a bone.

FIG. 35 shows a trap button 680 in accordance with aspects of the invention. In embodiments, the trap button 680 comprises a disc-shaped element having a through-hole 695 and a braided capture element 700 connected to an interior wall of the through-hole 695. The braided capture element 700 may be similar to braided capture element 410, and may have at least one end fused or otherwise connected to the interior wall of the through-hole 695 and a free-braid portion that is not directly connected to the interior wall of the through-hole 695. A portion of the disc-shaped element serves as the anchor of the female segment, and a wall surrounding the through hole serves as the hollow body of the female segment. The trap button 680 thus includes a hollow body with an anchor at one end of the hollow body and a braided capture element on an interior of the hollow body, and may be used as an alternative type of female segment in systems and methods according to aspects of the invention. The disc-shaped element of the trap button 680 may have a diameter 685 that is greater than a length 690 in order to provide a low profile, high surface area flange for engaging a tissue, i.e., as opposed to an elongate body (such as hollow body 350) which has a length much greater than its width. An exterior surface 702 of the disc-shaped element is configured to rest against tissue, and thus functions as an anchor surface for the trap button 680 against the tissue.

With continued reference to FIGS. 34 and 35, the bone anchor system may be used by first implanting the bone anchor 675 into a portion of bone in a patient's body. The needle 670 is then used to lead the suture 665, wedge 660, and insertion element 655 through a tissue that is to be connected to the bone associated with the bone anchor 675. The needle 670 is passed through the trap button 680, and the trap button is slid down the suture 665, wedge, 660, and insertion element 655, which movement operates to push the tissue toward the bone due to the trap button engaging the tissue. The braided capture element 700 permits the trap button 680 to be moved in one direction on the insertion element 655 (i.e., toward the bone anchor 675), but prevents the trap button from sliding back off the insertion element 655 (i.e., in a direction away from the bone anchor 675) by the same finger-trap principle already described herein.

FIG. 36 shows an additional embodiment of the bone anchor system that comprises two male segments 650 and 650' connected to a single bone anchor 675. The system also includes two trap buttons 680 and 680', one for each of the male members 650 and 650'. The male members 650 and 650' and the trap buttons 680 and 680' may be similar in construction and function to the male member 650 and trap button 680 described with respect to FIGS. 34 and 35. The embodiment shown in FIG. 36 may be used to connect two different tissues, or two different portions of the same tissue, to a bone.

FIG. 37 shows an embodiment of a knotless suture in accordance with aspects of the invention. In embodiments, the knotless suture comprises an insertion element 725 having a first end and a second end. The knotless suture includes a first introducer wedge 730a, first suture 735a, and first needle 740a at the first end of the insertion element 725. The knotless suture also includes a second introducer wedge 730b, second suture 735b, and second needle 740b at the second end of the insertion element 725. The insertion element 725, wedges 730a-b, sutures 735a-b, and needles 740a-b may be similar in construction and material(s) to the solid bodies, introducer wedges, sutures, and needles already described herein. For example, the insertion element 725 may comprise a monofilament or multifilament material, and may have a surface roughening similar to the surface roughening 420. As shown in FIG. 37, the knotless suture also includes two trap buttons 745a and 745b, which may be the same as trap button 680 in that they each comprise a disc-shaped element with a through-hole and a braided capture element in the through-hole.

Figure 38:
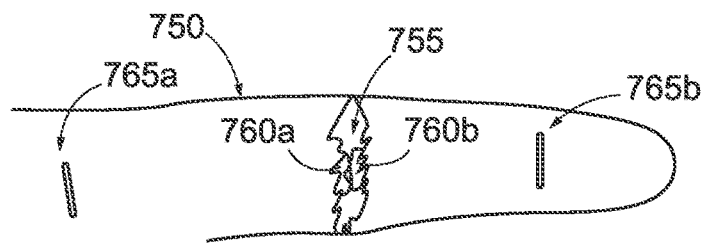

FIGS. 38-41 show an exemplary method of using the knotless suture of FIG. 37 in accordance with aspects of the invention. FIG. 38 shows a body part 750 (such as a finger) with a laceration 755 that exposes a first tissue 760a and a second tissue 760b, which may be ends of a cut tendon, for example. In embodiments, the surgeon makes a first incision 765a to locate an undamaged portion of the first tissue 760a, and makes a second incision 765b to locate an undamaged portion of the second tissue 760b.

Figure 39:
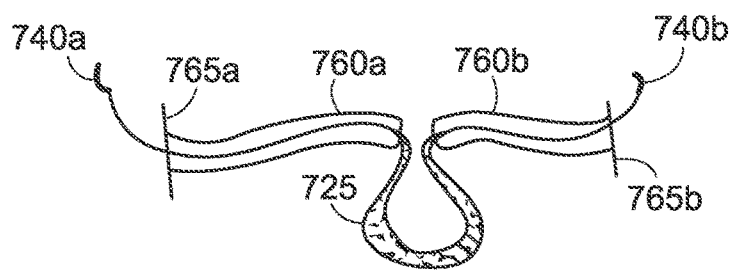

As depicted in FIG. 39, the surgeon passes the first needle 740a into the cut end of the first tissue 760a, moves the first needle 740a in retrograde fashion through the first tissue 760a toward the first incision 765a, and passes the first needle 740a through a sidewall of the first tissue 760a at the first incision 765a. The surgeon also passes the second needle 740b into the cut end of the second tissue 760b, moves the second needle 740b in retrograde fashion through the second tissue 760b toward the second incision 765b, and passes the second needle 740b through a sidewall of the second tissue 760b at the second incision 765b.

Figure 40:
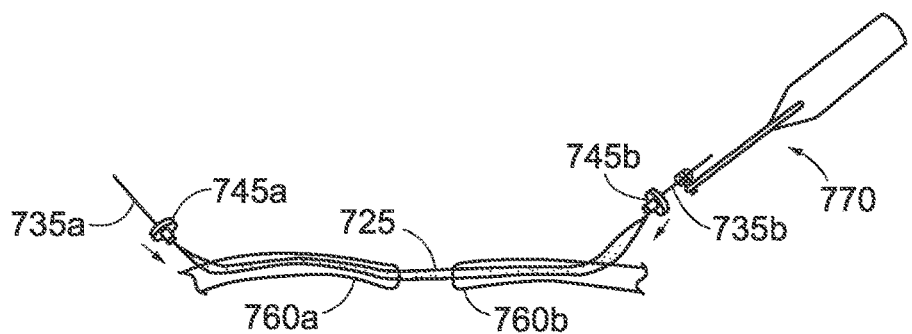

As shown in FIG. 40, the first needle 740a is cut off, the first suture 735a is passed through the through-hole of the first trap button 745a, and the first trap button 745a is slid down the first suture 735a and onto the insertion element 725. Similarly, the second needle 740b is cut off, the second suture 735b is passed through the through-hole of the second trap button 745b, and the second trap button 745b is slid down the second suture 735b and onto the insertion element 725. A pusher tool 770 may be used to advance the trap buttons 745a-b along the sutures 735a-b and onto the insertion element 725.

Figure 41:
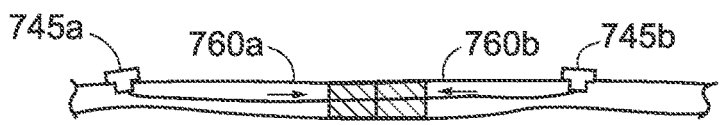

As depicted in FIG. 41, the first trap button 745a and the second trap button 745b are advanced along the insertion element 725 until the first tissue 760a and the second tissue 760b are moved into contact with one another. Any excess portions of the sutures 735a-b, wedges 730a-b, and insertion element 725 may be trimmed at locations outside of the trap buttons 745a-b. The trap buttons 745a-b engage the insertion element 725 using the braided capture elements and the finger-trap principle as described herein. The knotless suture system is advantageous in that it minimizes dissecting and/or exposing the wound at the point of injury (i.e., at the laceration 755), which achieves the repair with less swelling, faster recovery, and better outcomes.

Figure 42:
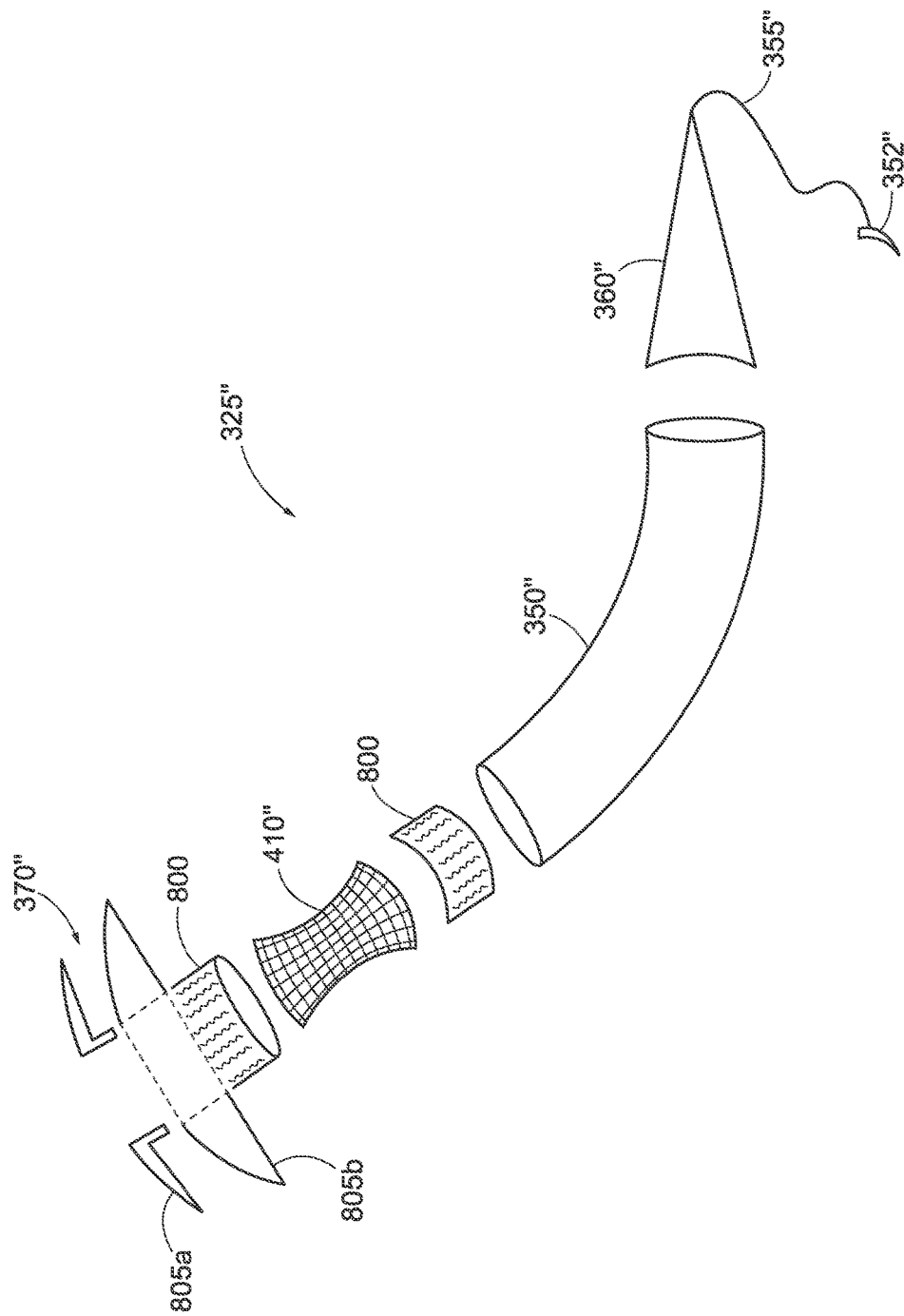
FIG. 42 shows an exploded view of an embodiment of a female segment similar to those depicted in FIGS. 21 and 28 in accordance with aspects of the invention.

FIG. 42 shows an exploded view of an embodiment of a female segment 325" similar to those depicted in FIGS. 26 and 30C. The female segment 325" includes a hollow element 350", wedge 360", suture 355", needle 352", and braided capture element 410" which may be the same as those elements described with respect to FIGS. 26 and 30C. According to aspects of the invention, a reinforcing material 800 is provided at one or both ends of the braided capture element 410". Destructive testing has been used to determine that the primary failure point is at the hollow tube immediately adjacent the ends of the braided capture element. Additionally, in embodiments, a reinforcing material 800 is provided at one or both ends of the braided capture element 410". The reinforcing material 800 may include, but is not limited to, stainless steel threads, fibers, or braids embedded in or otherwise fused to the hollow tube 350" at these locations. In a particular exemplary implementation, the reinforcing material 800 is secured between two pieces 805a and 805b of a two-piece anchor 370".

Figure 43:
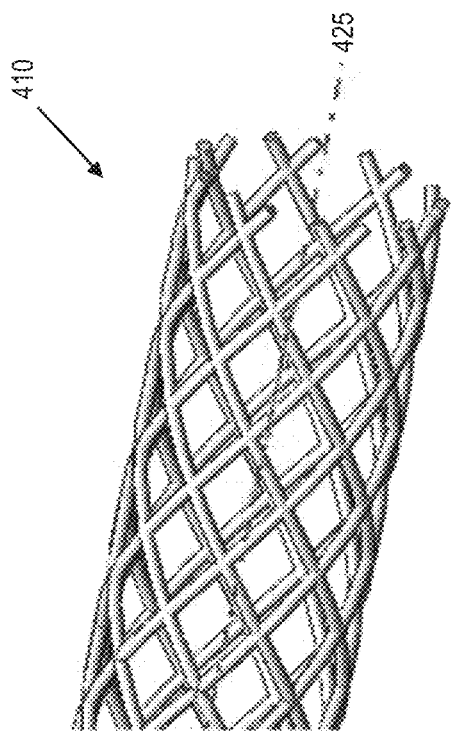
Figure 44:
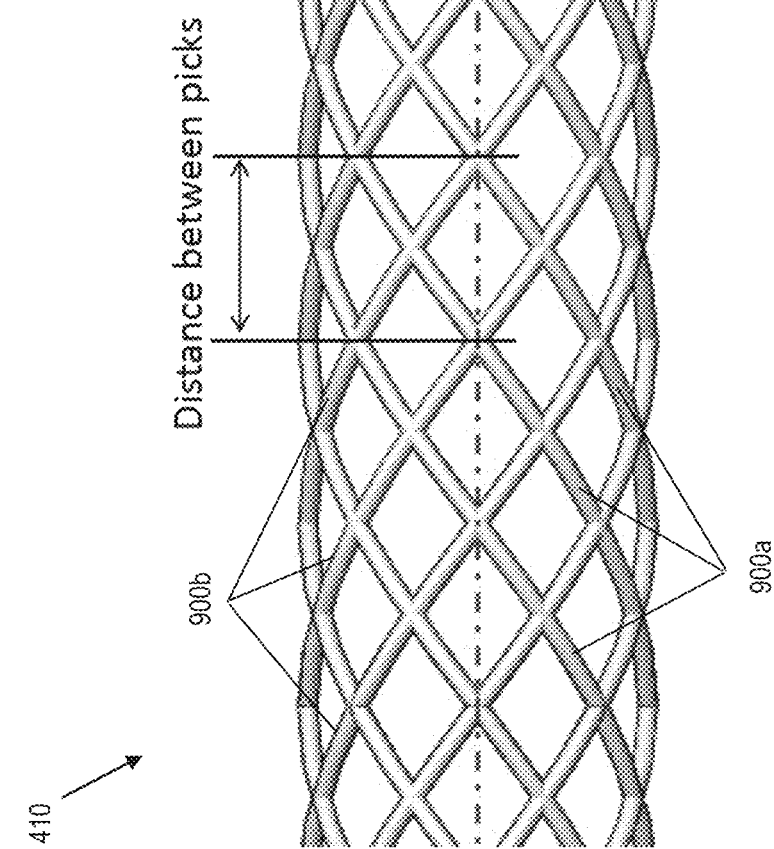

FIGS. 43-47 depict aspects of the braided capture element (e.g., braided capture element 410, etc.) used in various embodiments described with respect to FIGS. 26-42. As shown in FIGS. 43 and 44, a braided capture element 410 comprises first fibers 900a oriented in a first direction woven with second fibers 900b oriented in a second direction. The braided capture element 410 is tube-shaped and has a central longitudinal axis 425. The locations where one fiber crosses another is referred to as a pick. The braid can be designated by the number of picks per inch measured along the axis 425.

FIGS. 45-47 show how two different braids may have the same number of picks per inch, but have different inside diameters. For example, the braid 915 in FIG. 46 has 100 picks per inch and an inside diameter of 0.035 inches, while the braid 920 in FIG. 47 has 100 picks per inch and an inside diameter of 0.025 inches. The difference in inside diameter while having the same number of picks per inch causes braids 915 and 920 to have different lead angles between the fibers at the picks. For example, braid 915 has a lead angle of about 27°, while braid 920 has a lead angle of about 20°. One would intuitively think that for a same insertion element being inserted into braids 915 and 920 that the smaller diameter braid 920 would provide greater gripping force under the finger-trap principle. However, quite unexpectedly, the larger diameter braid 915 provides better gripping of a nylon insertion element than the smaller diameter braid 920. The inventors have found through empirical study that the gripping action provided by a braided capture element (e.g., element 410 gripping insertion element 380) is a function of all of the following parameters: radial force, coefficient of friction between the two members, lead angle of the braid, and amount of contact surface area. Based on this heretofore unknown understanding of the operative parameters in the finger-trap principle, the inventors have developed the following combination of materials and geometries that provides an above-average gripping force: a braided capture element (e.g., element 410) made of stainless steel wires having an outside diameter of about 0.002 inches; 12-16 wires in the braid; a lead angle of the wires in the braid in the range of 27° to 30°; wherein the braid has an outer diameter of about 0.020 inches when pulled taught; the braid has an inner diameter of in a range of 0.015 inches to 0.017 inches in its natural state, and is expandable to 0.021 inches; and an insertion element (e.g., insertion element 380) composed of a mono-filament or a multi-filament strand of braided and/or interwoven PEEK (polyetheretherketone), nylon, PET, or any other suitable metal and/or polymer material filaments.

All of the elements described herein are configured for use as medical implants, such as in a human body. Accordingly, any one or more of the elements described herein may be immunologically or chemically enhanced for use in the human body. For example, any one or more of the elements described herein may be immunologically or chemically enhanced to regulate, modify, or supplement tissue healing, and in particular tendon, ligament, or soft tissue healing. In but one particular example, any one or more of the elements described herein may be coated or impregnated or otherwise treated with growth hormone, antibiotic, etc.

The invention is not limited to the exemplary methods described herein. Instead, different processes may be practiced within the scope of the invention. For example, additional steps may be added, steps may be performed in a different order, etc. The systems and methods described herein according to aspects of the invention may be used in the following applications, although the invention is not limited to only these applications: closure of the sternum following cardiac surgery; closure of thoracic incisions following thoracic surgery; tendon repair; ligament repair; closure of abdominal fascia; intradermal closure of skin or subcutaneous tissue and fascia; facial rejuvenation; eyelid suspension; and, repair of bone fractures.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A system for fastening tissue, comprising:
a female segment comprising a hollow body, an first anchor at one end of the hollow body, and a braided capture element on an interior surface of the hollow body;
a free portion of the braided capture element is not directly connected to the interior surface of the hollow body;
a male segment comprising an insertion element, a second anchor at one end of the insertion element, a suture and needle connected to another end of the insertion element;
wherein, in an installed state, the female segment is structured and arranged to be within a first tissue with the first anchor contacting an exterior surface of the first tissue and anchoring the hollow body in the first tissue;
in the installed state, the male segment is structured and arranged to be within a second tissue with the second anchor contacting the second tissue and anchoring the insertion element in the second tissue;
the insertion element is structured and arranged to be inserted into and held within the hollow body in the installed state, thereby connecting the first tissue and the second tissue; and
the braided capture element restricts motion of the insertion element relative to the hollow body in the installed state.

2. The system of claim 1, wherein:
the braided capture element permits movement of the insertion element through the hollow body in a first direction; and
the braided capture element restricts movement of the insertion element through the solid hollow body in a second direction opposite the first direction.

3. The system of claim 1, wherein the braided capture element comprises a tube-shaped, helical braid.

4. The system of claim 1, wherein the braided capture element comprises a finger-trap structure.

5. The system of claim 1, wherein: at least one end of the braided capture element is directly connected to the interior surface of the hollow body.

6. The system of claim 1, wherein:
the insertion element comprises a roughened exterior surface or a material on the exterior surface; and
the roughened exterior surface or the material is structured and arranged to contact the braided capture element to cause the braided capture element to constrict around the insertion element when the insertion element begins to move in a predefined direction.

7. The system of claim 1, wherein:
a first portion of the insertion element has a circular cross sectional shape with a nominal outer diameter that is less than an inner diameter of the braided capture element; and
a second portion of the insertion element has a rounded rectangular cross sectional shape with a major dimension that is greater than the nominal outer diameter.

8. The system of claim 1, wherein
the female segment comprises a trap button comprising a disc-shaped element with a through-hole; and
the braided capture element is on an interior surface of the through-hole.

9. The system of claim 8, wherein the second anchor comprises a bone anchor that is structured and arranged to be inserted into bone.

10. The system of claim 9, wherein:
the male segment comprises two said insertion elements connected to the bone anchor;
each of the two said insertion elements includes a respective said suture and needle; and
the female segment comprises two said trap buttons corresponding to the two said insertion elements.

11. The system of claim 8, wherein:
the disc-shaped element has a diameter in a first direction;
the disc-shaped element has a length in a second direction aligned with the through-hole; and
the diameter is greater than the length.

12. The system of claim 8, wherein:
the disc-shaped element comprises a flange; and
the first anchor comprises an exterior surface of the disc-shaped element at the flange.

13. The system of claim 1, wherein in an uninstalled state the female segment is separate from the male segment.

14. The system of claim 1, wherein the braided capture element comprises a helically wound braid, the braid being configured such that applying opposing forces to the braid along its longitudinal axis outward from a center of the braid increases a length of the braid while also decreasing a circumference of the braid.

15. The system of claim 14, wherein the braid is configured such that the length of the braid is increased by reducing an angle between crossing fibers at their crossing points, which simultaneously reduces a radial distance from the longitudinal axis to the fibers, which decreases the circumference of the braid.

16. The system of claim 1, wherein:
the braided capture element comprises steel wires braided together; and
the insertion element comprises monofilament or multifilament and is composed of polymer material.

17. The system of claim 16, wherein a lead angle of the steel wires is in a range between 27° and 30°.

18. A system for fastening tissue, comprising:
a female segment comprising a trap button comprising: a disc-shaped element with a through-hole; a braided capture element connected to an interior wall of the through-hole;
a free portion of the braided capture element is not directly connected to the interior surface of the hollow body;
a male segment comprising: an insertion element; a bone anchor at a first end of the insertion element; and a suture and needle connected to a second end of the insertion element;
wherein the disc-shaped element has a diameter in a first direction;
the disc-shaped element has a length in a second direction aligned with the through-hole;
the second direction is different than the first direction;
the diameter is greater than the length;
in an uninstalled state the female segment is separate from the male segment;
the insertion element is configured to be passed through the through-hole of the trap button in a one direction to connect the male segment and the female segment in an installed state;

the braided capture element permits movement of the insertion element through the trap button in the one direction; and the braided capture element restricts movement of the insertion element through the trap button in a direction opposite the one direction.

19. The system of claim 18, wherein the braided capture element comprises a helically wound braid, the braid being configured such that applying opposing forces to the braid along its longitudinal axis outward from a center of the braid increases a length of the braid while also decreasing a circumference of the braid.

20. The system of claim 18, wherein:

the braided capture element comprises steel wires braided together; and the insertion element comprises monofilament or multi-filament and is composed of polymer material.

* * * * *